(12) United States Patent
Beaucage et al.

(10) Patent No.: US 6,762,298 B2
(45) Date of Patent: Jul. 13, 2004

(54) THERMOLABILE PHOSPHORUS PROTECTING GROUPS, ASSOCIATED INTERMEDIATES AND METHODS OF USE

(75) Inventors: Serge L. Beaucage, Silver Spring, MD (US); Andrzej Wilk, Bethesda, MD (US); Andrzej Grajkowski, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 162 days.

(21) Appl. No.: 09/792,799

(22) Filed: Feb. 23, 2001

(65) Prior Publication Data

US 2001/0044529 A1 Nov. 22, 2001

Related U.S. Application Data

(63) Continuation-in-part of application No. PCT/US00/04032, filed on Feb. 16, 2000.
(60) Provisional application No. 60/125,867, filed on Mar. 24, 1999.

(51) Int. Cl.$^7$ .................. C07H 21/00; C07H 21/02; C07H 21/04
(52) U.S. Cl. ................ 536/25.31; 536/25.3; 536/25.33; 536/25.34
(58) Field of Search .................. 536/25.33, 26.7, 536/26.8, 27.62, 27.81, 28.51, 28.53, 25.34, 26.74, 27.8, 25.3, 25.31

(56) References Cited

U.S. PATENT DOCUMENTS

| | | |
|---|---|---|
| 3,534,017 A | 10/1970 | Fujimoto et al. |
| 4,415,732 A | 11/1983 | Caruthers et al. |
| 4,417,046 A | 11/1983 | Hsiung |
| 4,458,066 A | 7/1984 | Caruthers et al. |
| 4,663,446 A | 5/1987 | Wright |
| 4,668,777 A | 5/1987 | Caruthers et al. |
| 4,725,677 A | 2/1988 | Köster et al. |
| 4,739,044 A | 4/1988 | Stabinsky |
| 4,757,141 A | 7/1988 | Fung et al. |
| 4,808,708 A | 2/1989 | Yoshida et al. |
| 4,816,569 A | 3/1989 | Miyoshi |
| 4,816,570 A | 3/1989 | Farquhar |
| 4,845,205 A | 7/1989 | Huynh Dinh et al. |
| 4,849,513 A | 7/1989 | Smith et al. |
| 4,950,745 A | 8/1990 | Ishido et al. |
| 4,973,679 A | 11/1990 | Caruthers et al. |
| 4,980,460 A | 12/1990 | Molko et al. |
| 5,026,838 A | 6/1991 | Nojiri et al. |
| 5,039,796 A | 8/1991 | Engels et al. |
| 5,071,974 A | 12/1991 | Groody |
| 5,091,519 A | 2/1992 | Cruickshank |
| 5,134,228 A | 7/1992 | Takaku |
| RE34,069 E | 9/1992 | Köster et al. |
| 5,166,330 A | 11/1992 | Engels et al. |
| 5,212,304 A | 5/1993 | Fung et al. |
| 5,214,135 A | 5/1993 | Srivastava et al. |
| 5,252,760 A | 10/1993 | Urdea et al. |
| 5,258,538 A | 11/1993 | Fung et al. |
| 5,324,831 A | 6/1994 | Marquez et al. |
| 5,332,845 A | 7/1994 | Ureda et al. |
| 5,348,868 A | 9/1994 | Reddy et al. |
| 5,428,148 A | 6/1995 | Reddy et al. |
| 5,430,138 A | 7/1995 | Urdea et al. |
| 5,449,602 A | 9/1995 | Royer et al. |
| 5,506,351 A | 4/1996 | McGee |
| 5,510,476 A | 4/1996 | Ravikumar et al. |
| 5,518,651 A | 5/1996 | Reddy et al. |
| 5,519,126 A | 5/1996 | Hecht |

(List continued on next page.)

FOREIGN PATENT DOCUMENTS

| | | |
|---|---|---|
| EP | 0 006 220 A1 | 1/1980 |
| EP | 0 090 789 A1 | 10/1983 |
| EP | 0 196 101 A2 | 10/1986 |
| EP | 0 219 342 A2 | 4/1987 |
| EP | 0 241 363 A1 | 10/1987 |
| EP | 0 323 152 A2 | 7/1989 |
| GB | 2 153 356 | 8/1985 |
| WO | WO 88/02004 A1 | 3/1988 |
| WO | WO 93/12132 A1 | 6/1993 |
| WO | WO 00/56749 A1 | 9/2000 |

OTHER PUBLICATIONS

Lefebvre et al. "Mononucleoside Phosphotriester Derivatives with S–Acyl–2–thioethyl Bioreversible Phosphate–Protecting Groups: Intracellular Delivery of 3'–Azido–2', 3'–dideoxythymidine 5'–Monophosphate" J. Med. Chem., 1995, 38 (20), 3941–3950.*

Wang et al. "A Stereoselective Synthesis of Dinucleotide Phosphorothioates, Using Chiral Indol–oxazaphosphorine Intermediates" Tetrahedron Letters, 1997, 38 (22), 3797–3800.*

Barone et al., *Nucl. Acids Res.*, 12(10), 4051–4061 (1984).

Beaucage et al., *Ann. New York Acad. Sci.*, 616, 483–485 (1990).

(List continued on next page.)

*Primary Examiner*—James O. Wilson
*Assistant Examiner*—Patrick Lewis
(74) *Attorney, Agent, or Firm*—Leydig, Voit & Mayer, Ltd.

(57) ABSTRACT

The invention provides a method of thermally deprotecting the internucleosidic phosphorus linkage of an oligonucleotide, which method comprises heating a protected oligonucleotide in a fluid medium at a substantially neutral pH, so as to deprotect the oligonucleotide.

The present invention further provides a method of synthesizing an oligonucleotide using the thermal deprotection method described above, and novel oligonucleotides and intermediates that incorporate the thermolabile protecting group used in accordance with the present invention.

12 Claims, 13 Drawing Sheets

U.S. PATENT DOCUMENTS

| | | | |
|---|---|---|---|
| 5,525,719 | A | 6/1996 | Srivastava et al. |
| 5,556,961 | A | 9/1996 | Foote et al. |
| 5,571,902 | A | 11/1996 | Ravikumar et al. |
| 5,574,146 | A | 11/1996 | Reddy et al. |
| 5,614,622 | A | 3/1997 | Iyer et al. |
| 5,616,700 | A | 4/1997 | Reddy et al. |
| 5,623,068 | A | 4/1997 | Reddy et al. |
| 5,639,867 | A | 6/1997 | Brill |
| 5,645,985 | A | 7/1997 | Froehler et al. |
| 5,646,265 | A | 7/1997 | McGee |
| 5,652,358 | A | 7/1997 | Pfleiderer et al. |
| 5,670,489 | A | 9/1997 | Baxter et al. |
| 5,681,940 | A | 10/1997 | Wang et al. |
| 5,700,919 | A | 12/1997 | Seliger et al. |
| 5,703,218 | A | 12/1997 | Urdea et al. |
| 5,703,223 | A | 12/1997 | Wickstrom et al. |
| 5,705,621 | A | 1/1998 | Ravikumar |
| 5,712,378 | A | 1/1998 | Wang |
| 5,714,597 | A | 2/1998 | Ravikumar et al. |
| 5,731,429 | A | 3/1998 | Reddy et al. |
| 5,763,599 | A | 6/1998 | Pfleiderer et al. |
| 5,866,700 | A | 2/1999 | Pfleiderer et al. |
| 5,889,165 | A | 3/1999 | Fodor et al. |
| 5,908,926 | A | 6/1999 | Pirrung et al. |
| 5,959,099 | A | 9/1999 | Cheruvallath et al. |
| 6,001,982 | A | 12/1999 | Ravikumar et al. |
| 6,022,963 | A | 2/2000 | McGall et al. |
| 6,043,060 | A | 3/2000 | Imanishi |
| 2001/0044529 | A1 | 11/2001 | Beaucage et al. |

OTHER PUBLICATIONS

Beaucage et al., *Current Protocols in Nucleic Acid Chemistry*, vol. 1 (Beaucage S.L., Bergstrom, D.E., Glick, G.D., Jones, R.A. eds), John Wiley and Sons: New York (2000) pp. 3.3.1–3.3.20.
Beaucage et al., *Tetrahedron*, 48(12), 2223–2311 (1992).
Beaucage et al., *Tetrahedron*, 49(28), 6123–6194 (1993).
Beaucage, *Methods in Molecular Biology, vol. 20: Protocols for Oligonucleotides and Analogs*, (S. Agrawal, ed.), Humana Press: Totowa, NJ (1993) pp. 33–61.
Bigg et al., *Synthesis*, 277–278 (Mar. 1992).
Boal et al., *Nucl. Acids Res.*, 24(15), 3115–3117 (1996).
Brown et al., *J. Chem. Soc. Chem. Commun.*, 891–893 (1989).
Gardrat et al., *J. Heterocyclic Chem.*, 27, 811–812 (1990).
Iyer et al., *J. Org. Chem.*, 55(15), 4693–4699 (1990).
Iyer, *Current Protocols in Nucleic Acid Chemistry*, vol. 1 (Beaucage S.L., Bergstrom, D.E., Glick, G.D. Jones R.A. eds); John Wiley and Sons: New York, (2000) pp. 2.1.1–2.1.17.
Martin, *Helv. Chim. Acta.*, 78, 486–504 (1995).
McBride et al., *J. Am. Chem. Soc.*, 108, 2040–2048 (1986).
Mizrakh et al., *Chemical Abstracts*, 83(23), 454 (1975).
Prakash et al., *Org. Lett.*, 2(25), 3995–3998 (2000).
Probst et al., *Makromol. Chem.*, 177, 2681–2695 (1976).
Pudovik et al., *Chemical Abstracts*, 79(11), 441 (1973).
Pudovik et al., *Chemical Abstracts*, 81(11), 484 (1974).
Regan et al., *Org. Prep. Proc. Int.*, 24(4), 488–492 (1992).
Saegusa et al., *Makromol. Chem.*, 177, 2271–2283 (1976).
Shibanuma et al., *Chem Pharm. Bull.*, 28(9), 2609–2613 (1980).
Smith et al., *Nucleosides & Nucleotides*, 15(10), 1581–1594 (1996).
Waldner et al., *Bioorg. Med. Chem. Letters*, 6(19), 2363–2366 (1996).
Wilk et al., *J. org. Chem.*, 62(20), 6712–6713 (1997).
Wilk et al., *J. Org. Chem.*, 64(20), 7515–7522 (1999).
Wincott, *Current Protocols in Nucleic Acid Chemistry*, vol. 1 (Beaucage S.L., Bergstrom, D.E., Glick, G.D, Jones, R.A. eds); John Wiley and Sons: New York, (2000) pp. 3.5.1–3.5.12.
Cao et al.; *Tetrahedron Letters*, 24(10), 1019–1020 (1983).
Grajkowski et al.; *Organic Letters*, 3(9), 1287–1290 (2001).
Gray et al.; *J. Am. Chem. Soc.*, 81, 4351–4355 (1959).
Guzaev et al.; *Tetrahedron Letters*, 41, 5623–5626 (2000).
Iyer et al.; *J. Org. Chem.*, 60, 5388–5389 (1995).
Iyer et al.; *Tetrahedron: Asymmetry*, 6 (5), 1051–1054 (1995).
Kawanobe et al.; *Chemistry Letters, Chem. Soc. of Japan*, 825–828 (1982).
Murphy et al.; *Tetrahedron*, 47(24), 4077–4088 (1991).
Tsuruoka et al.; *Tetrahedron Letters*, 40, 8411–8414 (1999).
Wilk et al.; *J. Am. Chem. Soc.*, 122, 2149–2156 (2000).
Wilk et al.; *Tetrahedron Letters*, 42, 5635–5639 (2001).
Wilk et al.; *J. Org. Chem.*, 67, 6430–6438 (2002).
Yang et al.; *Chem. Abs.*, 111, 97382x (1989).
Zhang et al.; *Chem. Abs.*, 126(2). 18939t (1997).
Finger et al., *J. Am. Chem. Soc.*, 81 (10), 2674–2675 (Jun. 2, 1959).
Mizrakh et al., *Zh. Obs. Khim.*, 45 (3), 549–552 (Mar., 1975).
Mizrakh et al., *Zh. Obs. Khim.*, 45 (7). 1469–1473 (Jul., 1975).
Mizrakh et al., *Zh. Obs. Khim.*, 45 (10), 2343–2344 (Oct., 1975).
Scremin et al., *J. Org. Chem.*, 59 (8), 1963–1966 (1994).
Somei et al., *Chem. Pharm. Bull.*, 28 (8), 2515–2518 (1980).
Stec et al., *Nucleic Acids Res.*, 19 (21), 5883–5888 (1991).
Weiner et al., *J. Org. Chem.*, 14, 868–872, (1949).

* cited by examiner

| X = O or S | | |
|---|---|---|
| Compound | Z | R¹ |
| 110 | NH | CH₃ |
| 111 | NCH₃ | CH₃ |
| 112 | NCH₃ | H |
| 113 | Z and R¹ together = CH₂CH₂CH₂ | |
| 114 | O | N(CH₃)₂ |
| 115 | CH₂ | CH₃ |
| 116 | CH₂ | NHCH₃ |
| 117 | CH₂ | NHC(CH₃)₃ |

| Compound | W | Z | R¹ |
|---|---|---|---|
| 102 | N(CH₂CH₃)₂ | NH | CH₃ |
| 103 | N(CH₂CH₃)₂ | NCH₃ | CH₃ |
| 104 | N(CH₂CH₃)₂ | NCH₃ | H |
| 105 | N(CH₂CH₃)₂ | Z and R¹ together = CH₂CH₂CH₂ | |
| 106 | N(CH₂CH₃)₂ | CH₂ | NHCH₃ |
| 107 | N(CH₂CH₃)₂ | CH₂ | NHC(CH₃)₃ |
| 108 | N(CH₂CH₃)₂ | O | N(CH₃)₂ |
| 109 | N(CH₂CH₃)₂ | CH₂ | CH₃ |

B = any protected nucleobase
S = solid support
DMTr = 4,4'-dimethoxytrityl
R[1'] = alkyl, aryl, aralkyl, fluoroalkyl

THERMOLABILE PHOSPHORUS PROTECTING GROUPS, ASSOCIATED INTERMEDIATES AND METHODS OF USE

CROSS-REFERENCE TO RELATED PATENT APPLICATIONS

This patent application is a continuation-in-part of copending international patent application No. PCT/US00/04032, filed Feb. 16, 2000, pending, which claims priority to U.S. provisional patent application No. 60/125,867, filed Mar. 24, 1999.

FIELD OF THE INVENTION

This invention pertains to thermolabile phosphate protecting groups, intermediates therefor and methods of using them in oligonucleotide synthesis.

BACKGROUND OF THE INVENTION

There are significant potential therapeutic applications for oligonucleotides. The therapeutic application of oligonucleotides is based on the selective formation of hybrids between antisense oligonucleotides and complementary nucleic acids, such as messenger RNAs (mRNAs). Such hybrids inhibit gene expression by preventing protein translation. Nuclease-resistant oligonucleotides are highly desirable in this regard. Nucleosides bearing phosphorothioate internucleotide linkages are well-known for such nuclease resistance and, thus, are undergoing rapid development.

In view of their significant potential therapeutic application, there is a high demand for improved methods of preparing oligonucleotides and analogues thereof. A number of methods for synthesizing oligonucleotides have been developed. The most commonly used synthetic method for the synthesis of thioated oligonucleotides is the phosphoramidite method with stepwise sulfurization (see, e.g., U.S. Pat. Nos. 4,415,732, 4,668,777, 4,973,679, 4,845,205, and 5,525,719). Essentially, a phosphate precursor is sulfurized such that a sulfur atom is substituted for one of the non-bridging oxygen atoms normally present in phosphodiesters. This method uses tricoordinated phosphorus precursors that normally produce products containing a mixture of different thioated oligonucleotide stereoisomers, primarily due to the use of non-stereoselective and non-stereospecific acid-catalyzed nucleophilic substitution reactions.

Protecting groups for internucleosidic phosphorus linkages and associated deprotection methods are well-known in the art, and have been described, for example, in U.S. Pat. Nos. 4,417,046, 5,705,621, 5,571,902 and 5,959,099. However, the methods presently used for removing internucleosidic phosphorus protecting groups are disadvantageous in that they employ harsh reagents, such as bases (e.g., ammonium hydroxide) and acids (e.g., trichloroacetic acid). Under these deprotection conditions, there is a greater risk of problems, such as by-product formation and degradation of the desired oligonucleotide, which make oligonucleotide purification more difficult and increase the overall cost, particularly in large-scale production processes. Moreover, the range of structural analogs that one can prepare is limited to those that are stable under the acidic and/or basic deprotection conditions that are commonly employed in the art.

Accordingly, there is a need for internucleosidic phosphorus protecting groups that can be removed under milder conditions and methods of making and using such protecting groups. Removal of such protecting groups should be fast and should be carried out under conditions that minimize the possibility for degradation of the desired oligonucleotide. In addition, the intermediates that introduce such protecting groups should be easy to synthesize inexpensively on a large scale. It is, therefore, of prime importance to develop low-cost, protected intermediates for oligonucleotide synthesis which are easy to synthesize, couple efficiently during stepwise synthesis, and are deprotected quickly in high yield under mild conditions.

The invention provides such protecting groups and methods. These and other objects and advantages of the invention, as well as additional inventive features, will be apparent from the description of the invention provided herein.

BRIEF SUMMARY OF THE INVENTION

The invention provides a method of thermally deprotecting an oligonucleotide. The method comprises heating an oligonucleotide of the formula:

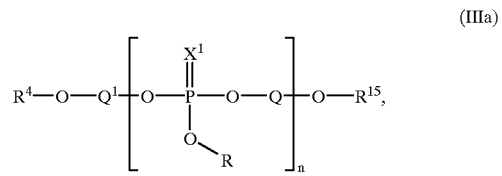

(IIIa)

in a fluid medium, at a substantially neutral pH, at a temperature up to about 100° C. to produce an oligonucleotide of the formula:

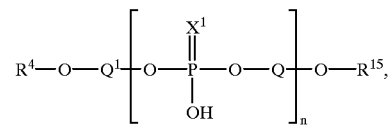

wherein R is a thermolabile protecting group of the formula:

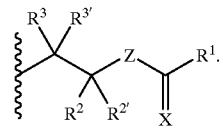

$R^1$ is H, $R^{1a}$, $OR^{1a}$, $SR^{1a}$ or $NR^{1a}R^{1a'}$, wherein $R^{1a}$ and $R^{1a'}$ are the same or different and each is H, an alkyl, an alkenyl, an alkynyl, a cycloalkyl, an aryl, or an aralkyl. Alternatively, when $R^1$ is $NR^{1a}R^{1a'}$, $R^{1a}$ and $R^{1a'}$, together with the nitrogen atom to which they are bonded, comprise a heterocycle. Substituent $X^1$ is O, S or Se and substituent X is O or S. Substituent Z is O, S, $NR^{2a}$, $CR^{2a}R^{2a'}$ or $CR^{2a}R^{2a'}CR^{2b}R^{2b'}$, wherein $R^{2a}$, $R^{2a'}$, $R^{2b}$ and $R^{2b'}$ are the same or different and each is H, an alkyl, an alkenyl, an alkynyl, a cycloalkyl, an aryl, or an aralkyl. Alternatively, $R^{1a}$ or $R^{1a'}$, in combination with any of $R^{2a}$, $R^{2a'}$, $R^{2b}$ or $R^{2b'}$, together with C=X of the protecting group to which they are bonded, comprise a ring containing from 3 to about 7 atoms in the skeleton thereof. $R^1$ is not $R^{1a}$ when Z is S, Z is not $CR^{2a}R^{2a'}$ or $CR^{2a}R^{2a'}CR^{2b}R^{2b'}$ when $R^1$ is $SR^{1a}$, and Z is not O or S when $R^1$ is H.

Substituents $R^2$, $R^{2'}$, $R^3$ and $R^{3'}$ are the same or different and each is H, an alkyl, an alkenyl, an alkynyl, a cycloalkyl, an aryl, or an aralkyl. Alternatively, $R^2$ or $R^{2'}$, in combination with $R^3$ or $R^{3'}$, together with the carbon atoms to which they are bonded, comprise a cyclic substituent of the formulae:

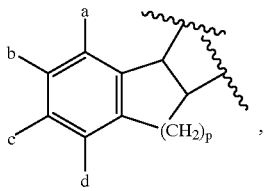

wherein p is an integer from 0–6 and a–d are the same or different and each is selected from the group consisting of H, an alkyl, a nitro, a dialkylamino, an alkoxy, an alkylthio, a cyano and a halogen, provided that the aromatic ring, which bears substituents a–d, is one carbon removed from the phosphate oxygen of formula (IIIa).

Substituents $R^1$, $R^{2a}$, $R^{2b}$, $R^{2b'}$, $R^2$, $R^{2'}$, $R^3$ or $R^{3'}$ can be unsubstituted substituted, as further described herein. Substituents $R^4$ and $R^{15}$ are the same or different and each is H, a hydroxyl protecting group, or a solid support.

Q and $Q^1$ are the same or different and each is a nucleoside, an oligonucleotide or an oligomer comprising an oligonucleotide. Variable n represents an integer from 1 to about 300. When n is greater than 1, each Q is independently selected.

The present invention further provides a novel compound selected from the group consisting of compounds of the formulae:

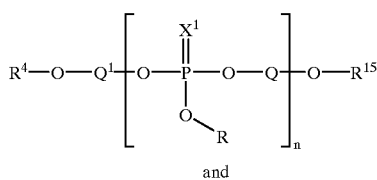

and

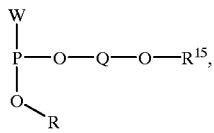

wherein R is a thermolabile protecting group as defined herein, $R^4$, $R^{15}$ and $X^1$ are as defined herein, and W is a dialkylamino group.

The present invention further provides method of producing an oligonucleotide. The method comprises:

(a) reacting a nucleophile of the formula:

$$R^4\text{—O—}Q^1\text{—OH};$$

with an electrophile of the formula:

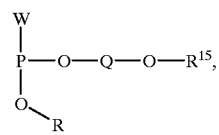

wherein R, $R^4$, Q, $Q^1$ and W are as defined herein, and $R^{15}$ is a protecting group, under conditions to displace W and produce an adduct comprising a tricoordinated phosphorus atom;

(b) reacting the product obtained in step (a) with a reagent selected from the group consisting of oxidizing agents, sulfurizing agents, and selenizing agents to produce a protected oligonucleotide of the formula:

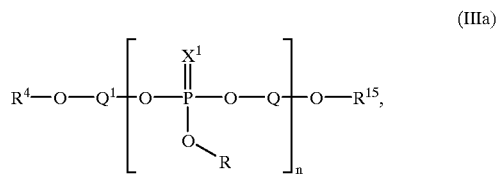

(IIIa)

wherein n=1;

(c) cleaving $R^{15}$ from the protected oligonucleotide from step (b) to produce a nucleophile;

(d) optionally repeating steps (a)–(c) until an oligomer of a specified length is obtained; and (e) thermally deprotecting the thermolabile protecting group R in accordance with the present invention.

DETAILED DESCRIPTION OF THE INVENTION

Figure 1A:
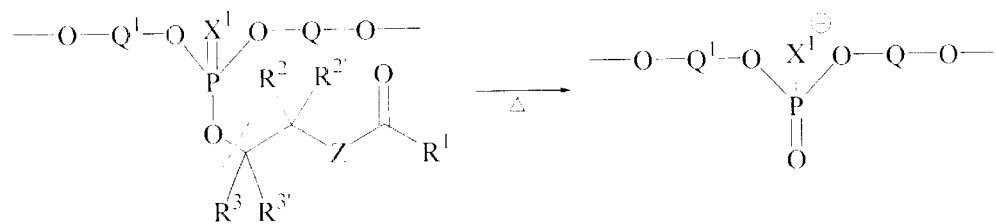
FIG. 1A generally illustrates the thermal deprotection of a tetracoordinated phosphorus internucleosidic linkage.

The present invention is predicated, at least in part, on the surprising and unexpected discovery of a method for thermally deprotecting the internucleosidic phosphorus linkage of an oligonucleotide, new thermolabile protecting groups that can be removed under such conditions and intermediates that incorporate them. The methods and protecting groups of the present invention simplify, and improve the efficiency and cost-effectiveness effectiveness of, oligonucleotide synthesis by avoiding the use of harsh reagents, such as alkaline or acidic reagents. In one embodiment, the present invention provides a method of deprotecting an oligonucleotide, which method comprises heating an oligonucleotide of the formula:

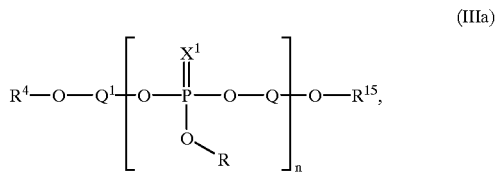

(IIIa)

in a fluid medium, at a substantially neutral pH, at a temperature up to about 100° C. to produce an oligonucleotide of the formula:

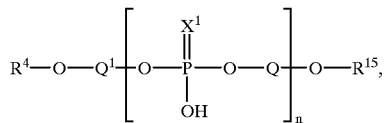

wherein:
R is a thermolabile protecting group of the formula:

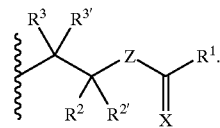

The deprotection method of the present invention can be performed in any suitable fluid medium. Suitable fluid media include, for example, liquid media and gaseous media. A preferred fluid medium comprises or contains water. Liquid media include, for example, solvents, preferably solvents that are liquid at room temperature. Suitable solvents include organic solvents and inorganic solvents.

Organic solvents preferably include those that are easily removed by evaporation. Preferably, the organic solvent is a polar organic solvent. Preferred polar organic solvents include, for example, acetonitrile; cyclic ethers such as, for example, dioxane and tetrahydrofuran; alcohols such as, for example, methanol, ethanol and isopropanol; mixtures thereof; and the like. Non-polar organic solvents such as, for example, hydrocarbons, e.g., hexane, cyclohexane and heptane; aromatic hydrocarbons, e.g., toluene and benzene; mixtures thereof, and the like can be included in the fluid medium, for example, as co-solvents.

Inorganic solvents include, for example, water. In a particularly preferred embodiment, the solvent is water or a mixture of one or more organic solvents and water.

The liquid medium can be a homogeneous solution or heterogeneous mixture, but is preferably a homogeneous solution. Most preferably, the liquid medium is a homogeneous solution that contains water as a co-solvent.

Suitable solvents include, for example, acetonitrile/water mixtures ranging from about 10:1 (v/v) to about 1:10 (v/v) acetonitrile/water. Suitable acetonitrile/water mixtures include, for example, about 9:1 (v/v) acetonitrile/water, about 5:1 (v/v) acetonitrile/water, about 2:1 (v/v) acetonitrile/water, about 1:1 (v/v) acetonitrile/water, about 1:2 (v/v) acetonitrile/water, about 1:5 (v/v) acetonitrile/water, and about 1:9 (v/v) acetonitrile/water.

Suitable solvents also include, for example, dioxane/water mixtures ranging from about 10:1 (v/v) to about 1:10 (v/v) dioxane/water. Suitable dioxane/water mixtures include, for example, about 9:1 (v/v) dioxane/water, about 5:1 (v/v) dioxane/water, about 2:1 (v/v) dioxane/water, about 1:1 (v/v) dioxane/water, about 1:2 (v/v) dioxane/water, about 1:5 (v/v) dioxane/water, and about 1:9 (v/v) dioxane/water.

Suitable solvents also include other organic solvent/water mixtures, e.g., using the ratios described herein. Other suitable solvents include organic solvents, such as, for example, acetonitrile, dioxane, mixtures thereof, and the like, that contain a trace amount of water (e.g., from about 0.05–2 wt. %, from about 0.1–2 wt. %, from about 0.5–2 wt. %, from about 1–2 wt. %, and the like).

The method of the present invention can be performed in a gaseous medium, most preferably a gaseous medium that contains water in a gaseous or fluid state (e.g., steam, hot water mist or vapor, or the like). The gaseous medium also can include the gaseous phases of any of the organic solvents or solvent mixtures described herein. In a particularly preferred embodiment, the method of the present invention includes contacting the oligonucleotide of formula (IIIa) (e.g., bound to a solid support) with steam.

As indicated above, the method of the present invention is carried at a substantially neutral pH. As utilized herein, the term "substantially neutral pH" means a pH in the range from about 5.5–7.5, preferably from about 6–7.5, most preferably about 7 (e.g., about 7.0–7.4). Optionally, a buffer can be added to the solvent system to maintain a substantially neutral pH throughout the course of the deprotection reaction. Suitable buffers include, for example, phosphate buffers, trialkylammonium acetate buffers (e.g., 0.1 M triethylammonium acetate), and the like.

The deprotection method of the present invention is preferably performed at a temperature that is sufficient to remove the protecting group at a rate that is practical for commercial scale production (e.g., about 3 hours or less), but should be low enough to avoid thermal degradation of the desired oligonucleotide. Typically, the deprotection is performed at a temperature up to about 100° C. (at about 100° C. or less), e.g., from above about ambient temperature (e.g., above about 20–25° C.) to about 100° C. Preferably, the deprotection is performed at a temperature from about 50–100° C., more preferably from about 60–100° C., still more preferably from about 70–100° C., most preferably from about 80–100° C. About 90° C. or about 100° C. is especially preferred. When a liquid solvent medium is used, the deprotection is preferably performed from about 50–90°

C., more preferably from about 60–90° C., still more preferably from about 70–90° C., even still more preferably from about 80–90° C., and most preferably at about 90° C. However, in some circumstances, it may be desirable to carry out the deprotection at somewhat higher temperatures (e.g., up to about 110° C., e.g., from about 100–105° C.).

The structure of the thermolabile protecting group (substituent R of formula IIIa) can vary considerably in terms of different combinations of $R^1$, $R^2$, $R^{2'}$, $R^3$, $R^{3'}$, Z and X, while maintaining thermal lability. In other words, the bond linking protecting group R to the non-bridging phosphate, phosphorothioate or phosphoroselenoate oxygen can be thermally cleaved using different combinations of $R^1$, $R^2$, $R^{2'}$, $R^3$, $R^{3'}$, Z and X.

While $R^1$ can be any suitable substituent, $R^1$ preferably is H, $R^{1a}$, $OR^{1a}$, $SR^{1a}$ or $NR^{1a}R^{1a'}$, wherein $R^{1a}$ and $R^{1a'}$ are the same or different and each is H, an alkyl, an alkenyl, an alkynyl, a cycloalkyl, an aryl, or an aralkyl. Alternatively, when $R^1$ is $NR^{1a}R^{1a'}$, $R^1$ and $R^{1a'}$, together with the nitrogen atom to which they are bonded, comprise a heterocycle containing from 3 to about 7 atoms in the ring skeleton thereof.

Preferably, $X^1$ is O, S or Se; X is O or S; and Z is O, S, $NR^{2a}$, $CR^{2a}R^{2a'}$ or $CR^{2a}R^{2a'}CR^{2b}R^{2b'}$, wherein $R^{2a}$, $R^{2a'}$, $R^{2b}$ and $R^{2b'}$ are the same or different and each is H, an alkyl, an alkenyl, an alkynyl, a cycloalkyl, an aryl, or an aralkyl. Alternatively, $R^{1a}$ or $R^{1a'}$, in combination with any of $R^{2a}$, $R^{2a'}$, $R^{2b}$ or $R^{2b'}$, together with C=X of the protecting group to which they are bonded, comprise a ring containing from 3 to about 7 atoms in the skeleton thereof.

It is preferred that thioesters are not utilized in the methods or the protecting groups of the present invention as they are believed to have a tendency to hydrolyze rather easily in the presence of water. Thus, when Z is S, it is preferred that $R^1$ is not $R^{1a}$. Similarly, when $R^1$ is $SR^{1a}$, Z is not $CR^{2a}R^{2a'}$ or $CR^{2a}R^{2a'}C^{R2b}R^{2b'}$. Further, it is preferred that formate esters or formate thioesters are not utilized in the methods or the protecting groups of the present invention as they also are believed to have a tendency to hydrolyze rather easily in the presence of water. Thus, when $R^1$ is H, it is preferred that Z is not O or S.

While $R^2$, $R^{2'}$, $R^3$ and $R^{3'}$ can be any suitable substituent, $R^2$, $R^{2'}$, $R^3$ and $R^{3'}$ preferably are the same or different and each is H, an alkyl, an alkenyl, an alkynyl, a cycloalkyl, an aryl, or an aralkyl. Alternatively, $R^2$ or $R^{2'}$, in combination with $R^3$ or $R^{3'}$, together with the carbon atoms to which they are bonded, can comprise a cyclic substituent of the formula:

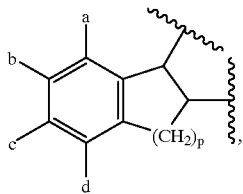

wherein p is an integer from 0–6 and a–d are the same or different and each is selected from the group consisting of H, an alkyl, a nitro, a dialkylamino, an alkoxy, an alkylthio, a cyano and a halogen, provided that the aromatic ring, which bears substituents a–d, is one carbon removed from (i.e., is benzylic relative to) the phosphate oxygen of formula (IIIa).

The foregoing substituents can be unsubstituted or substituted. Preferably, $R^1$, $R^{2a}$, $R^{2a'}$, $R^{2b}$, $R^{2b'}$, $R^2$, $R^{2'}$, $R^3$ or $R^{3'}$ is unsubstituted or substituted. Preferably, $R^1$, substituents, which are the same or different, selected from the group consisting of $OR^8$, CN, $NO_2$, $N_3$, and a halogen, wherein $R^8$ is H or an alkyl.

Substituents $R^4$ and $R^{15}$ are the same or different and each is preferably H, a hydroxyl protecting group, or a solid support. Substituent $Q^1$ represents a nucleoside, an oligonucleotide or an oligomer comprising an oligonucleotide. The variable n is an integer from 1 to about 300, preferably from about 3 to about 200, more preferably from about 10 to about 40, and most preferably from about 15 to about 25. Substituent Q represents a nucleoside, an oligonucleotide or an oligomer comprising an oligonucleotide. When n is an integer greater than 1, each Q is independently selected, i.e., each Q in each monomeric unit can be the same or different.

As utilized herein, the term "alkyl" means a straight-chain or branched-chain alkyl radical which, unless otherwise specified, contains from about 1 to about 20 carbon atoms, preferably from about 1 to about 10 carbon atoms, more preferably from about 1 to about 8 carbon atoms, and most preferably from about 1 to about 6 carbon atoms. Examples of such alkyl radicals include methyl, ethyl, propyl, isopropyl, n-butyl, sec-butyl, isobutyl, tert-butyl, pentyl, isoamyl, hexyl, octyl, dodecanyl, and the like.

The term "alkenyl" means a straight-chain or branched-chain alkenyl radical, which has one or more double bonds and, unless otherwise specified, contains from about 2 to about 20 carbon atoms, preferably from about 2 to about 10 carbon atoms, more preferably from about 2 to about 8 carbon atoms, and most preferably from about 2 to about 6 carbon atoms. Examples of alkenyl radicals include vinyl, allyl, 1,4-butadienyl, isopropenyl, and the like.

The term "alkynyl" means a straight-chain or branched-chain alkynyl radical, which has one or more triple bonds and contains from about 2 to about 20 carbon atoms, preferably from about 2 to about 10 carbon atoms, more preferably from about 2 to about 8 carbon atoms, and most preferably from about 2 to about 6 carbon atoms. Examples of alkynyl radicals include ethynyl, propynyl (propargyl), butynyl, and the like.

The terms "alkylamino" and "dialkylamino" mean an alkyl or a dialkyl amine radical, wherein the term "alkyl" is defined as above. Examples of alkylamino radicals include methylamino ($NHCH_3$), ethylamino ($NHCH_2CH_3$), n-propylamino, isopropylamino, n-butylamino, isobutylamino, sec-butylamino, tert-butylamino, n-hexylamino, and the like. Examples of dialkylamino radicals include dimethylamino ($N(CH_3)_2$), diethylamino ($N(CH_2CH_3)_2$), di-n-propylamino, diisopropylamino, di-n-butylamino, diisobutylamino, di-sec-butylamino, di-tert-butylamino, di-n-hexylamino, and the like.

The term "cycloalkyl" means a monocyclic alkyl radical, or a polycyclic alkyl which comprises one or more alkyl carbocyclic rings, which can be the same or different when the polycyclic radical has 3 to about 10 carbon atoms in the carbocyclic skeleton of each ring. Preferably, the cycloalkyl has from about 4 to about 7 carbon atoms, more preferably from about 5 to about 6 carbons atoms. Examples of monocyclic cycloalkyl radicals include cyclopropyl, cyclobutyl, cyclopentyl, cyclohexyl, cycloheptyl, cyclodecyl, and the like. Examples of polycyclic cycloalkyl radicals include decahydronaphthyl, bicyclo[5.4.0]undecyl, adamantyl, and the like.

The term "aryl" refers to an aromatic carbocyclic radical, as commonly understood in the art, and includes monocyclic and polycyclic aromatics such as, for example, phenyl and naphthyl radicals, which radicals are, unless indicated otherwise, unsubstituted or substituted with one or more substituents selected from the group consisting of a halogen, an alkyl, an alkoxy, an amino, a cyano, a nitro, and the like. Preferably, the aryl has one or more six-membered carbocyclic rings including, for example, phenyl, naphthyl, and biphenyl, and are unsubstituted or substituted as set forth herein.

The term "aralkyl" means alkyl as defined herein, wherein an alkyl hydrogen atom is replaced by an aryl as defined herein. Examples of aralkyl radicals include benzyl, phenethyl, 1-phenylpropyl, 2-phenylpropyl, 3-phenylpropyl, 1-naphthylpropyl, 2-naphthylpropyl, 3-naphthylpropyl, 3-naphthylbutyl, and the like.

The terms heterocycle and heterocyclic refer to both heterocycloalkyls and heteroaryls. The term "heterocycloalkyl" means a cycloalkyl radical as defined herein (including polycyclics), wherein at least one carbon of a carbocyclic ring is substituted with a heteroatom such as, for example, O, N, or S. The heterocycloalkyl optionally has one or more double bonds within a ring, and may be aromatic, but is not necessarily aromatic. The heterocycloalkyl preferably has 3 to about 10 atoms (members) in the skeleton of each ring, more preferably from about 3 to about 7 atoms, more preferably from about 5 to about 6 atoms. Examples of heterocycloalkyl radicals include epoxy, aziridyl, oxetanyl, tetrahydrofuranyl, ribose, dihydrofuranyl, piperidinyl, piperazinyl, pyranyl, morpholinyl, and the like.

The term "heteroaryl" means a radical defined by an aromatic heterocyclic ring as commonly understood in the art, including monocyclic radicals such as, for example, imidazole, thiazole, pyrazole, pyrrole, furane, pyrazoline, thiophene, oxazole, isoxazole, pyridine, pyridone, pyrimidine, cytosine, 5-methylcytosine, thymine, pyrazine, and triazine radicals, and polycyclics such as, for example, quinoline, isoquinoline, indole, purine, adenine, guanine, N6-methyladenine, and benzothiazole radicals, which heteroaryl radicals are unsubstituted or substituted with one or more substituents, which are the same or different, selected from the group consisting of a halogen, an alkyl, an alkoxy, an amino, a cyano, a nitro, and the like. The heteroaryl preferably has 3 to about 10 atoms (members) in the ring skeleton of each ring, more preferably from about 3 to about 7 atoms, more preferably from about 5 to about 6 atoms.

It will be appreciated that the heterocycloalkyl and the heteroaryl substituents can be coupled to the compounds of the present invention via a heteroatom, such as nitrogen (e.g., 1-imidazolyl), or via a carbon atom (e.g., 4-thiazolyl). It will also be appreciated that heteroaryls, as defined herein, are not necessarily "aromatic" in the same context as phenyl is aromatic, although heteroaryls nonetheless demonstrate physical and chemical properties associated with aromaticity, as the term is understood in the art.

The term "carboxyl" means any functional group with a carbonyl backbone, and includes functional groups such as, for example, a carboxylic acid, an esters (e.g., ethoxycarbonyl), and amides (e.g., benzamido).

The term "nucleoside" includes all modified and naturally occurring nucleosides, including all forms of furanosides found in nucleic acids. Naturally occurring nucleosides include, for example, adenosine, guanosine, cytidine, thymidine, and uridine.

Nucleoside "derivatives" or "analogs" include synthetic nucleosides as described herein. Nucleoside derivatives also include nucleosides having modified base moieties, with or without protecting groups. Such analogs include, for example, deoxyinosine, 2,6-diaminopurine-2'-deoxyriboside, 5-methyl-2'-deoxycytidine, and the like. The base rings most commonly found in naturally occurring nucleosides are purine and pyrimidine rings. Naturally occurring purine rings include, for example, adenine, guanine, and $N^6$-methyladenine. Naturally occurring purine rings include, for example, cytosine, thymine, and 5-methylcytosine. The compounds and methods of the present invention include such base rings and synthetic analogs thereof, as well as unnatural heterocycle-substituted base sugars, and even acyclic substituted base sugars. Moreover, nucleoside derivatives include other purine and pyrimidine derivatives, for example, halogen-substituted purines (e.g., 6-fluoropurine), halogen-substituted pyrimidines, $N^6$-ethyladenine, $N^6$-(alkyl)-cytosines, 5-ethylcytosine, and the like.

The term "oligonucleotide" as used herein includes linear oligomers of natural or modified nucleosides, and modified ologonucleotides, as described herein. Oligonucleotides include deoxyribonucleosides, ribonucleosides and anomeric forms thereof, and the like. Oligonucleotides are typically linked by phoshodiester bonds, or the equivalent thereof, ranging in size from a few monomeric units (e.g., 2–4) to several hundred monomeric units. Preferably, the oligonucleotides of the present invention are oligomers of naturally-occurring nucleosides ranging in length from about 12 to about 60 monomeric units, and more preferably, from about 15 to about 30 monomeric units. Whenever an oligonucleotide is represented by a sequence of letters, such as "AGTC" it will be appreciated that the nucleotides are in the 5'–3' orientation from left to right.

In accordance with the present invention, Q and/or $Q^1$ can be a natural nucleoside or a modified/unnatural nucleoside. Q and/or $Q^1$ also can be an oligomer comprising one or more natural or modified/unnatural nucleosides. Modified nucleosides can be obtained, for example, by any suitable synthetic method known in the art for preparing nucleosides, derivatives, or analogs thereof. Modified nucleosides include, but are not limited to, chemically modified nucleosides used as building blocks for "labeled" oligonucleotides, or suitable precursors or analogs used in the preparation of such modified nucleosides. Various chemically modified nucleosides are described, for example, in Smith et al., *Nucleosides & Nucleotides*, 15(10), 1581–1594 (1996) ("Smith et al."). Smith et al. describes the synthesis of nucleosides (and oligomers which include such nucleosides) in which the base ring is replaced by a carboxylic acid to which is appended various "labeling" groups (e.g., biotin, cholesterol, fluorenylmethoxycarbonyl (Fmoc), and trifluoroacetyl) via a modified amide linker. Modified nucleosides also include other chemically modified nucleosides, for example, nucleosides described in Smith et al. in which the base ring is replaced by a hydroxyethyl, a cyano, or a carboxylic acid (including esters and amides thereof). Modified nucleosides further include nucleosides in which the base ring is replaced by a cyclic substituent, for example, an aryl, a cycloalkyl, a heterocycloalkyl, or a heteroaryl (other than a base naturally occurring in nucleosides).

Q and/or $Q^1$ also include oligonucleotides, which can be natural or modified. Modified oligonucleotides include, for example, oligonucleotides containing a modified nucleoside (as described herein), oligonucleotides containing a modified internucleotide linkage, or oligonucleotides having any combination of modified nucleosides and internucleotide linkages (even if a natural nucleoside is present in the oligomer chain). Oligonucleotides whose nucleosides are connected via modified internucleotide linkages can be found, for example, in Waldner et al., *Bioorg. Med. Chem. Letters*, 6, 19, 2363–2366 (1996) ("Waldner et al."), which describes the synthesis of oligonucleotides containing various amide internucleotide linkages.

The term "oligomer comprising a nucleoside" as utilized herein means an oligomer in which at least one of the monomeric units comprises nucleoside, and at least one of the other monomeric units is not a nucleoside. For example, one of the monomeric units in the oligomer can be an amino acid, an organic spacer (e.g., an aliphatic or aromatic spacer, an alkylene glycol, or the like), or a carbohydrate (e.g., a sugar). Moreover, one of the non-nucleoside units of the oligomer can itself be oligomeric, for example, a peptide, an oligosaccharide, a polyalkylene glycol, or the like.

It will be appreciated that protecting groups (sometimes referred to as a blocking groups) other than the thermolabile protecting groups described herein can be utilized in accordance with the present invention. Generally, the term "protecting group," as used herein, means a substituent, functional group, salt, ligand, or the like, which is bonded (e.g., via covalent bond, ionic bond, or complex) to a potentially reactive functional group and prevents the potentially reactive functional group from reacting under certain reaction conditions. Potentially reactive functional groups include, for example, amines, carboxylic acids, alcohols, double bonds, and the like. Preferably, the protecting group is stable under the reaction conditions for which the protecting group is employed, and also can be removed under reasonably mild deprotection conditions. It will be appreciated that any additional protecting groups to be used in accordance with the present invention should be chosen based on the type of substituent that is being protected. Thus, in general, it is not uncommon to use a different protecting group for each of a phosphite oxygen, a phosphate oxygen, an amine, a thiol, a hydroxyl, and the like. It will also be appreciated that the choice of protecting groups will depend on other factors such as, for example, the reaction conditions employed in a particular synthetic step, the pH, the temperature, and the relative reactivities of the reactants and/or products.

Protecting groups for hydroxyls include, for example, silyl ethers (e.g., trimethylsilyl, triethylsilyl, tert-butyldimethylsilyl, tert-butyldiphenylsilyl, dimethylphenylsilyl, and diphenylmethylsilyl), benzyl carbonates, trityl, monomethoxytrityl, dimethoxytrityl, esters (e.g., acetate, benzoate, and the like), pixyl, tert-butyloxycarbonyl, 9-fluorenylmethyloxycarbonyl (Fmoc), a tetrahydropyranyl group, and the like. When the hydroxyl is a sugar hydroxyl, preferred protecting groups include, for example, pixyl, acetyl, 9-fluorenylmethyloxycarbonyl (Fmoc), t-butyldimethylsilyl (TBDMS), trityl, monomethoxytrityl ("MMT" or "MMTr"), dimethoxytrityl ("DMT" or "DMTr"), and the like. Protecting groups for nitrogen include, for example, amides (e.g., trifluoroacetyl, benzoyl, and isobutyryl), carbamates (e.g., tert-butyloxycarbonyl and N-benzyloxycarbonyl), trityl, and the like.

When an amine to be protected is part of a nucleoside base ring, suitable protecting groups can include amides, for example, benzoyl, isobutyryl, and the like. Other protecting groups are defined in the literature. See, e.g., Iyer, Current Protocols in Nucleic Acid Chemistry, Vol.1 (Beaucage S. L., Bergstrom, D. E., Glick, G. D. Jones R. A. eds); John Wiley and Sons: New York, 2000, pp. 2.1.1–2.1.17; Beaucage, et al., Tetrahedron, 48, 2223–2311 (1992); and McBride et al., J. Am. Chem. Soc., 108, 2040–2048 (1986).

Suitable protecting groups also include, for example, 2-[N,N-(dialkylamino)oxy]ethyl (Prakash et al., Org. Lett., 2, 2995–3998 (2000)), a (2-methoxy)ethoxy (Martin, Helv. Chim. Acta., 78, 486–504 (1995)), triisopropylsilyloxymethyl and those groups defined by Wincott, Current Protocols in Nucleic Acid Chemistry, Vol.1 (Beaucage S. L., Bergstrom, D. E., Glick, G. D. Jones R. A. eds); and John Wiley and Sons: New York, 2000, pp. 3.5.1–3.5.12.

Any suitable solid support can be used in accordance with the present invention. Solid supports are commonly known in the art and include, for example, organic solid supports (e.g., crosslinked polystyrene) and inorganic solid supports. Preferably, the solid support is inorganic, and is more preferably a silica support. It will be appreciated that the solid support includes all linkers, spacers, arms, and other moieties (organic or inorganic) known in the art for manipulating attachment to a solid support. It will also be appreciated that the solid support can be bonded to the molecule directly, without using any of the aforesaid linkers, spacers, arms, or other connecting moieties. Some aspects of the invention are common with known approaches to solid phase synthesis of oligonucleotides, for example, selection of suitable protecting groups, selection of suitable solid phase supports, and the like. Consequently, considerable guidance in making such selections in the context of the present invention can be found in literature, e.g. Beaucage et al., Tetrahedron, 49, 6123–6194 (1993). Desirably, $R^4$ and $R^{15}$ are not both solid supports.

Preferably, Q or $Q^1$ comprises a nucleoside of the formula:

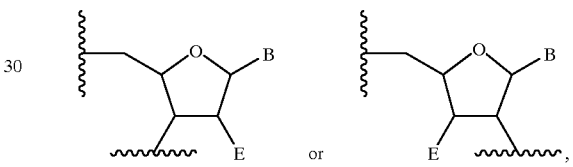

wherein B is a labeling group, an alkyl, an alkenyl, an alkynyl, a cycloalkyl, an aryl, a heteroaryl, a heterocycloalkyl, an aralkyl, an amino, an alkylamino, a dialkylamino, a purine, a pyrimidine, adenine, guanine, cytosine, uracil, or thymine, wherein B is unsubstituted or substituted with one or more substituents, which are the same or different, selected from the group consisting of a nucleobase protecting group, $R^{11}$, $OR^{11}$, $NHR^{11}$, $NR^{11}R^{12}$, an amidine (e.g., N=CH—$NR^{11'}R^{12'}$ or N=C(alkyl)—$NR^{11'}R^{12'}$), CN, $NO_2$, $N_3$, and a halogen, wherein $R^{11}$ and $R^{12}$ are the same or different and each is H, an alkyl or an acyl, and $R^{11'}$ and $R^{12'}$ are the same or different and each is an alkyl. Alternatively, $R^{11'}$ and $R^{12'}$, together with the nitrogen atom to which they are bonded, form a heterocycle containing 3 to about 7 atoms in the ring skeleton thereof. Substituent E is preferably H, a halogen, $OR^{13}$, $NHR^{13}$, or $NR^{13}R^{14}$, wherein $R^{13}$ and $R^{14}$ are the same or different and each is H, a protecting group, an alkyl, or an acyl. In a preferred embodiment, Q and/or $Q^1$ is a nucleoside substituent of the formula:

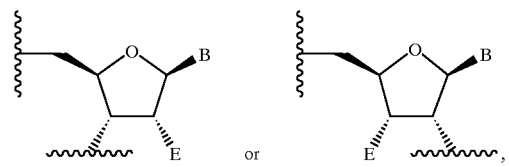

wherein B and E are as defined herein.

It will be appreciated that certain combinations of $R^1$, $R^2$, $R^2$, $R^3$, $R^{3'}$, Z and X, can be chosen to promote thermal cleavage of the bond linking the protecting group to the non-bridging phosphate, phosphorothioate or phosphoroselenoate oxygen. For example, $R^3$ can be chosen from among substituents that may increase the lability of the bond linking the organic moiety to the non-bridging phosphate, phosphorothioate or phosphoroselenoate oxygen, e.g., an electron-withdrawing group or a cation-stabilizing group, e.g., an aryl, preferably a phenyl. Alternatively, $R^3$ and/or $R^{3'}$ can be a substituent that makes the carbon to which it is attached less hindered (e.g., $R^3$ and $R^{3'}$ are H) and, possibly, more susceptible to a thermally-mediated deprotection mechanism, e.g., internal displacement by the C=X residue.

In one embodiment, $R^1$ is H, an alkyl or a heterocycle defined by $NR^{1a}R^{1a'}$, wherein $R^{1a}$ and $R^{1a'}$, together with the nitrogen atom to which they are bonded, comprise a heterocycle containing from 3 to about 7 atoms in the ring skeleton thereof. In another embodiment $X^1$ is S. In yet another embodiment, Z is $CR^{2a}R^{2a'}$ or $CR^{2a}R^{2a'}CR^{2b}R^{2b'}$, wherein $R^{2a}$, $R^{2a'}$, $R^{2b}$ and $R^{2b'}$ are same or different and each is H or an alkyl. In still another embodiment, $R^2$ or $R^{2'}$ is H or an alkyl. In yet another embodiment, $R^3$ or $R^{3'}$ is H, an alkyl or an aryl. It will be appreciated that other combinations of substituents not specifically described herein also can be used in connection with the method of the present invention. Examples of specific protecting groups (R) used in accordance with the present invention include protecting groups of the formulae:

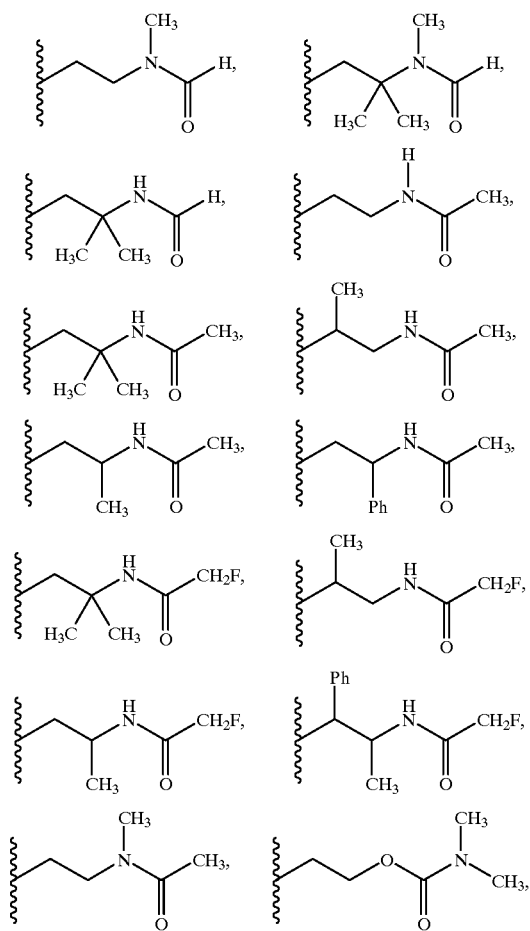

-continued

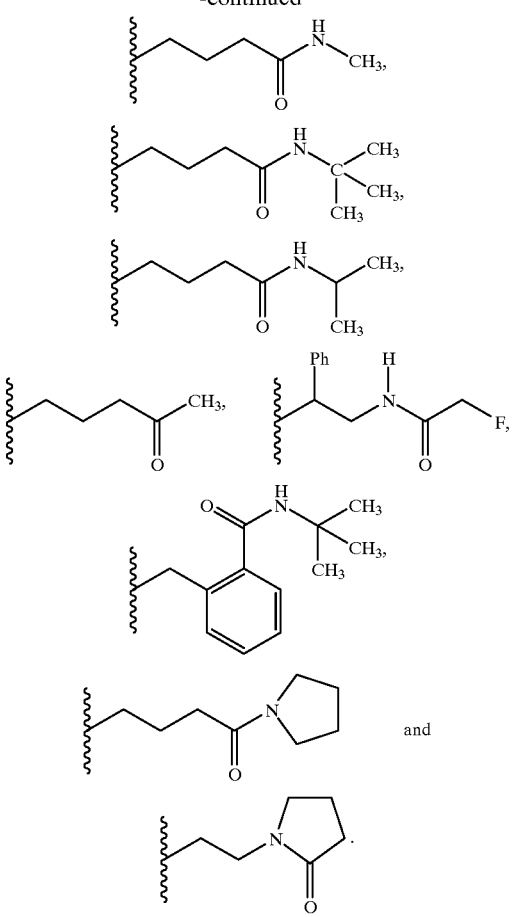

and

The thermal deprotection method of the present invention is generally illustrated in FIG. 1A. The thermal cleavage of the bond that links the protecting group to the non-bridging phosphate, phosphorothioate or phosphoroselenoate oxygen is indicated by the dotted lines shown in FIG. 1A. See also FIG. 1B. As indicated above, thermal cleavage can be advantageous in that the use of harsh chemicals, such as ammonium hydroxide, is avoided. As such, thermal cleavage provides a mild alternative that can be used in the production of monomeric, oligomeric, or polymeric compounds, particularly those that incorporate nucleoside monomers, which are substituted with substituents that are chemically labile under standard acidic or basic deprotection conditions.

Figure 1B:
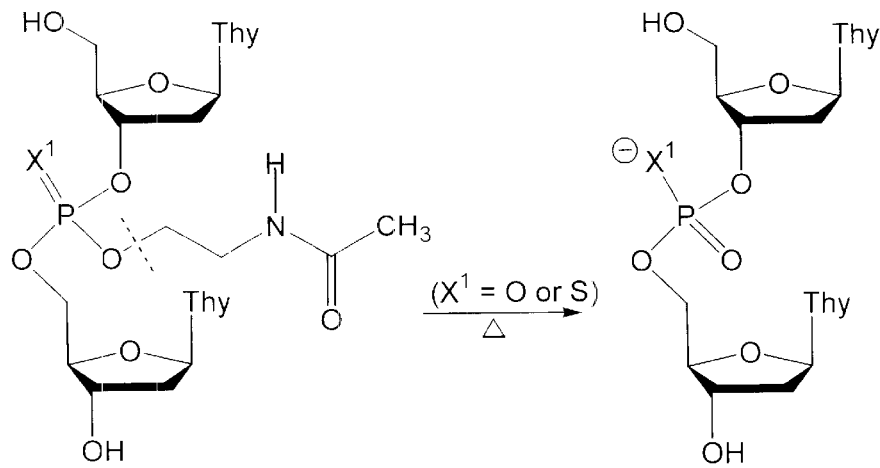
FIG. 1B illustrates the thermal deprotection of a phosphate/thiophosphate internucleosidic linkage.
Figure 1C:
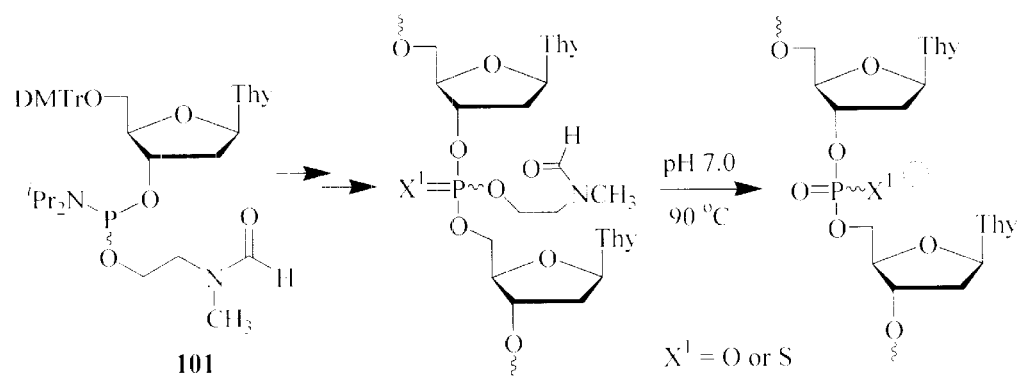
FIG. 1C illustrates the thermal deprotection of the phosphate/thiophosphate internucleosidic linkage of an oligonucleotide prepared from a phosphoramidite precursor.
Figure 1D:
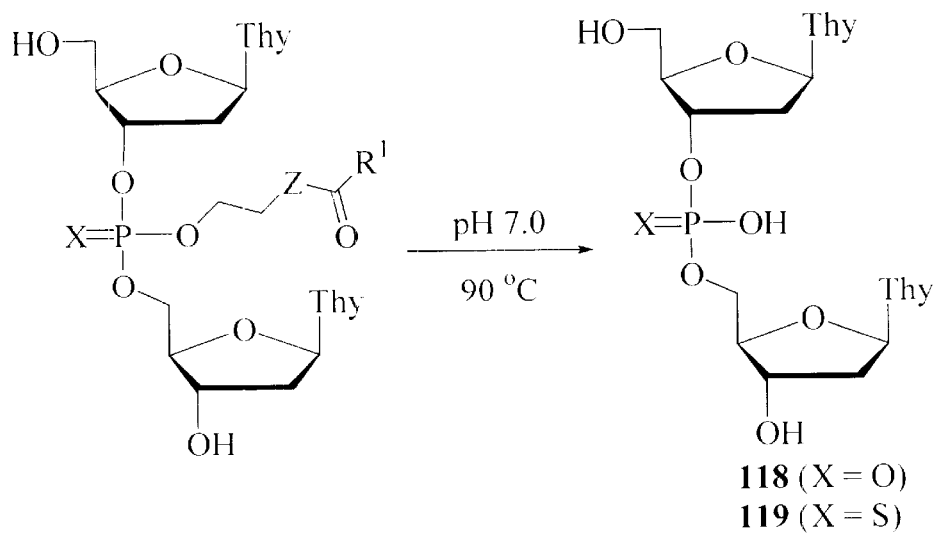
FIG. 1D illustrates the thermal deprotection of various thermolabile phosphate/thiophosphate protecting groups.

The thermal cleavage of various protecting groups is shown in FIGS. 1B–1D. FIG. 1B illustrates the thermal cleavage of an acetamide protecting group. The thermal cleavage illustrated in FIG. 1B (i.e., wherein $X^1$ is O or S), for example, can be carried out to completion in about 80 minutes at about 80° C. FIG. 1C illustrates the thermal deprotection of a formamide protecting group. FIG. 1D illustrates the thermal deprotection of various protecting groups with various combinations of substituents Z and $R^1$.

The thermolabile protecting groups of the present invention can be employed in oligonucleotide synthesis methods that are well-known in the art. For example, oligonucleotides that incorporate thermolabile protecting groups can be obtained from phosphoramidite precursors such as, for example, compound 101 (FIG. 1C). The phosphoramidite precursors can be prepared using well-known synthetic methods, e.g., as illustrated in FIG. 2A.

Figure 2A:
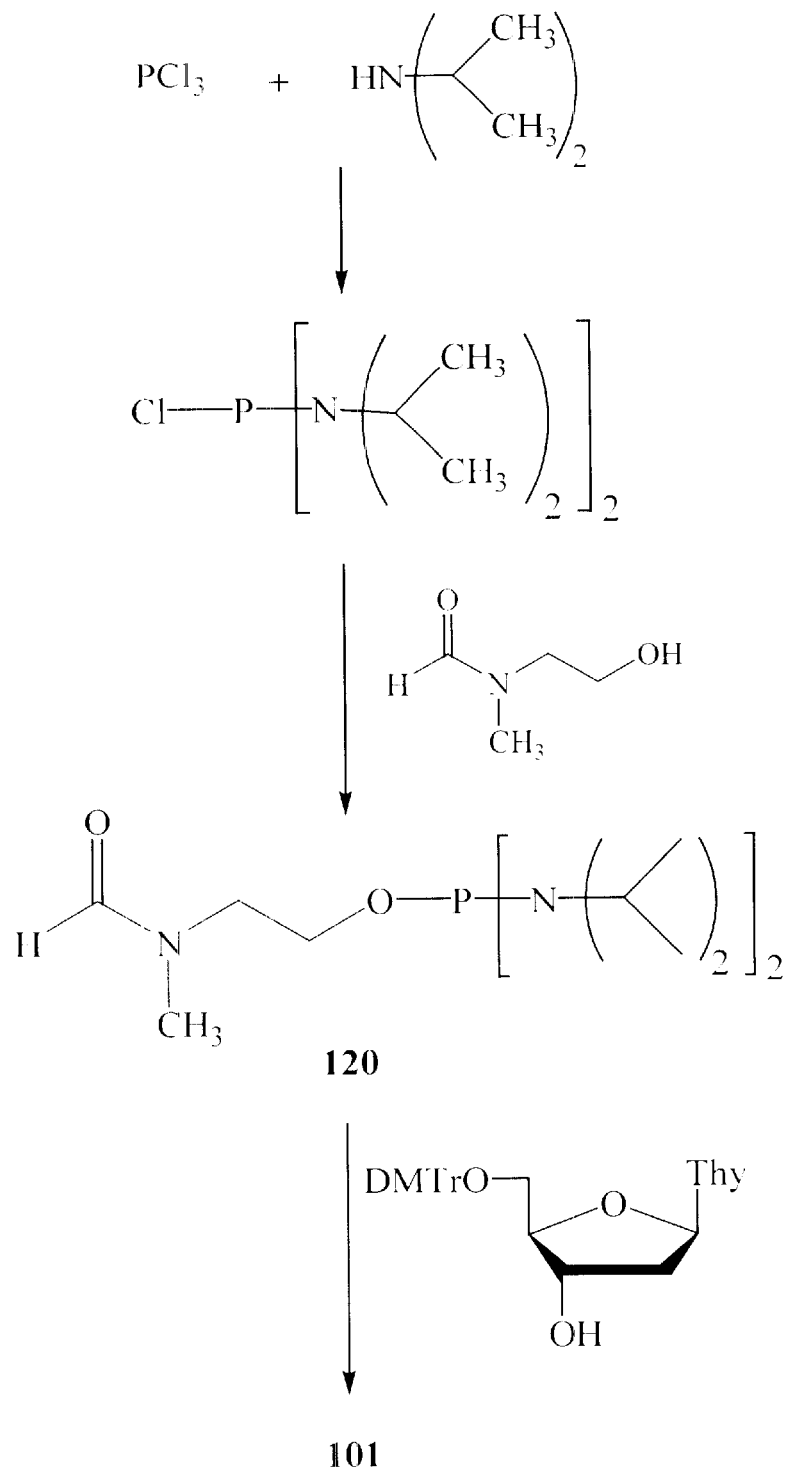
FIG. 2A illustrates the synthesis of various phosphoramidite precursors.

The synthesis shown in FIG. 2A can be carried out, for example, by adding anhydrous N,N-diisopropylamine to a solution of phosphorus trichloride in dry benzene to produce bis(N,N-diisopropylamino)chlorophosphine, and reacting it in situ with 2-(N-formyl-N-methyl) aminoethan-1-ol to produce phosphordiamidite 120 in about 73% yield. Phosphordiamidite 120 can then be reacted with a suitably protected nucleophile, such as 5'-O-(4,4'-dimethoxytrityl)-2'-deoxythymidine (Barone et al., *Nucl. Acids Res.*, 12, 4051–4061 (1984)) to produce deoxyribonucleoside phosphoramidite 101 (FIG. 2A).

Phosphoramidite precursors incorporating structurally diverse thermolabile protecting groups can be prepared in a manner similar to that shown in FIG. 2A, using structurally diverse alcohol derivatives. Such alcohol derivatives include, for example, N-acetylethanolamine (commercially available from Aldrich Chemical Co., Milwaukee, Wis.), 2-(N-acetyl-N-methyl)aminoethanol (Saegusa et al., *Makromol. Chem.*, 177, 2271–2283 (1976)), 2-(N-formyl-N-methyl)aminoethanol (Shibanuma et al., *Chem Pharm. Bull.*, 28, 2609–2613 (1980)), 1-(2-hydroxyethyl)-2-pyrrolidinone (commercially available from Aldrich Chemical Co., Milwaukee, Wis.), N-methyl-4-hydroxybutyramide (Wilk et al., *J. Org. Chem.*, 64, 7515–7522 (1999)), N-tert-butyl-4-hydroxybutyramide (Bigg et al., *Synthesis*, 277–278 (1992)), N,N-dimethyl-1-hydroxyethylcarbamate (Probst et al., *Makromol. Chem.*, 177, 2681–2695 (1976)), 3-acetyl-1-propanol (commercially available from Aldrich Chemical Co., Milwaukee, Wis.), and the like. Alternatively, phosphoramidite precursors can be prepared by reacting a suitably protected nucleophile, such as 5'-O-(4,4'-dimethoxytrityl)-2'-deoxythymidine, with hexaethylphosphorus triamide and diethylammonium tetrazolide in dry acetonitrile for 30 min at 25° C. to produce the corresponding deoxyribonucleoside 3'-O-phosphordiamidite, which can be reacted in situ with an equimolar amount of any of the alcohol derivatives described above (Wilk et al., *J. Org. Chem.*, 62, 6712–6713 (1997)).

Figure 2B:
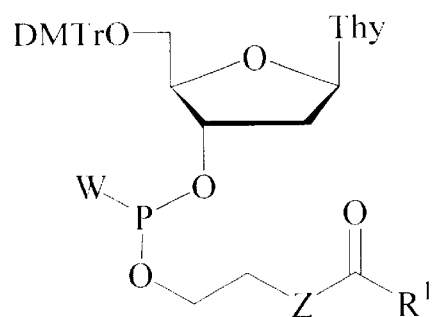
FIG. 2B illustrates the structures of various phosphoramidite precursors.

Exemplary phosphoramidite precursors of the present invention are shown in FIG. 2B. Dinucleoside phosphotriesters 110–117 (FIG. 1D) can be made from the corresponding phosphoramidite precursors shown in FIG. 2B, for example, by activating with 1H-tetrazole, and manually coupling to a suitably protected nucleophile, such as, e.g., 5'-unprotected thymidine covalently attached to long-chain alkylamine-controlled pore glass (LCAA-CPG). Standard aqueous iodine oxidation or sulfurization, e.g., by 3H-1,2-benzodithiol-3-one 1,1-dioxide (Beaucage et al., *Ann. New York Acad. Sci.*, 616, 483–485 (1990); Iyer et al., *J. Org. Chem.*, 55, 4693–4699 (1990); and Regan et al., *Org. Prep. Proc. Int.*, 24, 488–492 (1992)), followed by release from LCAA-CPG by treatment with pressurized methylamine gas for 3 min at 25° C. (Boal et al., *Nucl. Acids Res.*, 24, 3115–3117 (1996)), produces dinucleoside phosphotriesters 110–117 (FIG. 1D). Removal of the phosphate protecting groups from purified dinucleoside phosphotriesters 110–112 and 115–117 (X=O) in aqueous solvents (e.g., water or an eluent from chromatographic purification, e.g., a water/acetonitrile mixture), at about pH 7 (without the aid of concentrated ammonium hydroxide), occurs in less than 3 h at -90° C. affording the corresponding dithymidylyl monophosphate 118 in essentially quantitative yields. Removal of the phosphate protecting groups from phosphotriesters 113 and 114 under these conditions typically occurs in about 14 h and 4 h, respectively. Removal of the thiophosphate protecting groups from thiophosphate triesters 110, 112, 114, 116 and 117 (X=S) in aqueous solvents, at about pH 7, occurs in less than 3 h at -90° C. affording the corresponding dithymidylyl monothiophosphate 119 in essentially quantitative yields. Removal of the thiophosphate protecting groups from thiophosphate triesters 111, 113 and 115 also is accomplished under these conditions, although a desulfurization side reaction has been observed in some cases.

Oligonucleoside phosphotriesters bearing protecting group R can be readily prepared from phosphoramidite precursors of the present invention using standard methods that are well-known in the art, e.g., solid-phase synthesis. Thermal deprotection of oligonucleoside phosphotriesters bearing protecting group R is accomplished using mild conditions, for example, by heating at about 90° C. or less, for 3 h or less, in an aqueous solvent such as, for example, water or 2:3 (v/v) acetonitrile/water, with or without a buffer (e.g., 0.1M triethylammonium acetate), at pH 7.0, to afford the corresponding oligonucleotide in high yield. Using this procedure, oligonucleotides such as $dT_{18}$ and $d(AG)_{10}$ have been prepared in high yield and high purity.

The present invention further provides a method of producing an oligonucleotide, which method comprises:

(a) reacting a nucleophile of the formula:

$$R^4\text{—}O\text{—}Q^1\text{—}OH$$

with an electrophile of the formula:

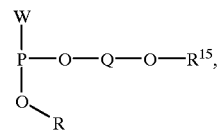

(IIIb)

wherein $R^{15}$ is a protecting group as defined herein and W is a dialkylamino group that is displaced by the nucleophile, under conditions to displace W and produce an adduct comprising a tricoordinated phosphorus atom;

(b) reacting the product obtained in step (a) with a reagent selected from the group consisting of oxidizing agents, sulfurizing agents, and selenizing agents to produce a protected oligonucleotide of the formula:

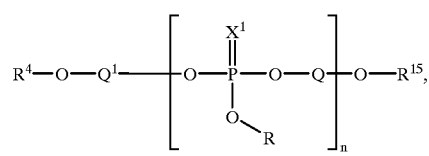

(IIIa)

wherein n=1;

(c) cleaving $R^{15}$ from the protected oligonucleotide from step (b) to produce a nucleophile;

(d) optionally repeating steps (a)–(c) until an oligomer of a specified length is obtained; and (e) heating the product from step (c) or (d) in a fluid medium, at a substantially neutral pH, at a temperature up to about 100° C. to produce a deprotected oligonucleotide of the formula:

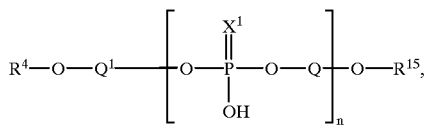

wherein R is a thermolabile protecting group of the formula:

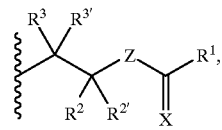

wherein W, $R^1$, $X^1$, X, Z, $R^2$, $R^{2'}$, $R^3$, $R^{3'}$, $R^4$, $Q^1$, Q and n are as defined above The present invention further provides novel thermolabile internucleosidic phosphorus protecting groups and novel intermediates that incorporate such protecting groups. Preferably, the present invention provides a compound selected from the group consisting of compounds of the formula:

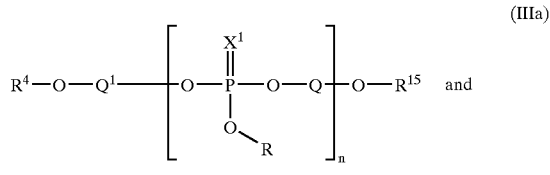

wherein R is a thermolabile protecting group of the formula:

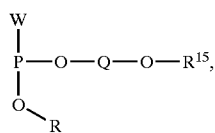

wherein W, $R^1$, $X^1$, X, Z, $R^2$, $R^{2'}$, $R^3$, $R^{3'}$, $R^4$, $R^{15}$, $Q^1$, Q and n are as provided, however, that when $R^1$ is not H, Z is not $NR^{2a}$, wherein $R^{2a}$ is H, an alkyl, an alkenyl, an alkynyl, a cycloalkyl, an aryl, or an aralkyl.

Preferably, Q or $Q^1$ in the compound of the present invention comprises a nucleoside of the formula:

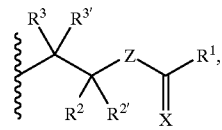

wherein B and E are as defined above. In a preferred embodiment, Q and/or $Q^1$ is a nucleoside substituent of the formula:

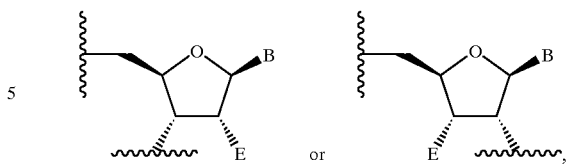

wherein B and E are as defined above.

As indicated above, certain combinations of $R^1$, $R^2$, $R^{2'}$, $R^3$, $R^{3'}$, Z and X, can be chosen to promote thermal cleavage of the bond linking the protecting group to the non-bridging phosphate, phosphorothioate or phosphoroselenoate oxygen. In one embodiment, $R^1$ is H, an alkyl or a heterocycle defined by $NR^{1a}R^{1a'}$, wherein $R^{1a}$ and $R^{1a'}$, together with the nitrogen atom to which they are bonded, comprise a heterocycle containing from 3 to about 7 atoms in the ring skeleton thereof. In another embodiment $X^1$ is S. In yet another embodiment, Z is $CR^{2a}R^{2a'}$ or $CR^{2a}R^{2a'}CR^{2b}R^{2b'}$, wherein $R^{2a}$, $R^{2a'}$, $R^{2b}$ and $R^{2b'}$ are same or different and each is H or an alkyl. In still another embodiment, $R^2$ or $R^{2'}$ is H or an alkyl. In yet another embodiment, $R^3$ or $R^{3'}$ is H, an alkyl or an aryl. It will be appreciated that other combinations of substituents not specifically described herein also can be used in accordance with the present invention. Examples of novel protecting groups used in accordance with the present invention include protecting groups of the formulae:

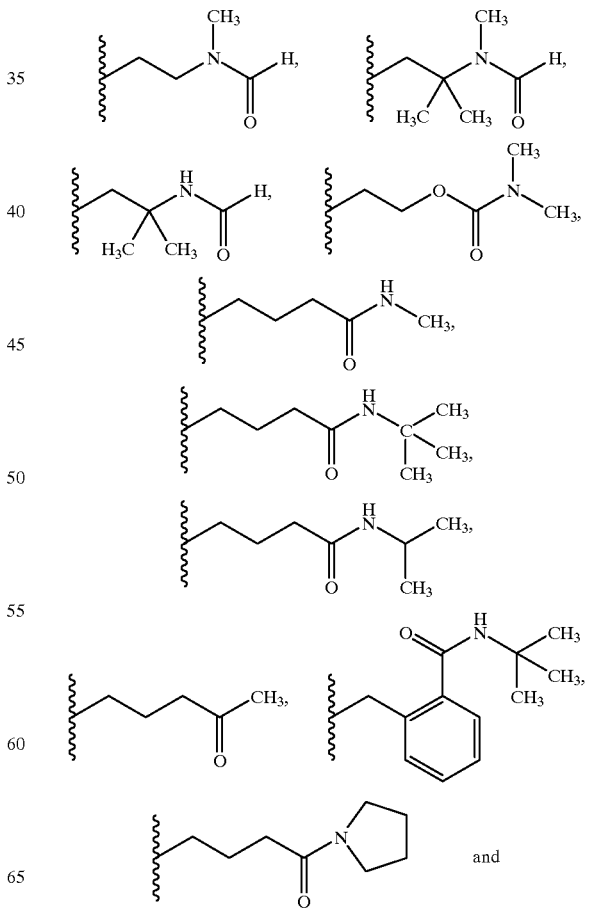

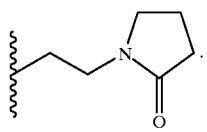

The phosphoramidite coupling approach in oligonucleotide synthesis is well-known in the art and typically involves displacement of an amino functionality on phosphorus. Acidic conditions are required for the displacement of the amino functionality. The phosphorus-nitrogen bond in a standard phosphoramidite is labile under acidic conditions (even when a mild acid such as tetrazole is used), invariably resulting in epimerization of the phosphorus atom in the resulting coupled adduct. Although attempts have been made to control the extent of epimerization in coupling reactions using phosphoramidites, there is inevitably some epimerization, which promotes the formation of diastereomers. Even if the formation of undesired diastereomers occurs in minute quantities, the overall yield of the target product decreases exponentially.

This problem can be overcome by utilizing N-acylphosphoramidites as alternative coupling vehicles, for example, to couple nucleoside-containing fragments. See WO 00/56749. N-acylphosphoramidites are advantageous in that the coupling reactions can be performed without any epimerization at phosphorus. Using N-acylphosphoramidites, oligonucleotides bearing the thermolabile protecting group R can be readily prepared. Exemplary oligomers that can be prepared using the N-acylphosphoramidites described herein include, e.g., oligonucleoside phosphotriesters of the formula:

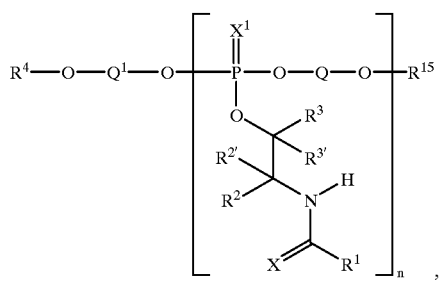

wherein $R^1$, $X^1$, $X$, $R^2$, $R^{2'}$, $R^3$, $R^{3'}$, $R^4$, $R^{15}$, $Q^1$, Q and n are as defined above. Oligonucleotides bearing other thermolabile protecting groups also can be prepared from other N-acylphosphoramidites (e.g., acyclic N-acylphosphoramidites). Moreover, when N-acylphosphoramidites are used, post-coupling reactions and transformations, for example, oxidation, sulfurization, and deprotection, occur without epimerization at the phosphorus atom. Thus, utilizing N-acylphosphoramidites provides for the facile production of P-chiral oligomeric or polymeric products, with complete control of stereochemistry with respect to the phosphorus atom. Moreover, stereochemistry can be controlled for tricoordinated and tetracoordinated phosphorus atoms.

In view of the above, the N-acylphosphoramidites that can be utilized in accordance with the present invention are preferably selected from the group consisting of compounds of the formulae:

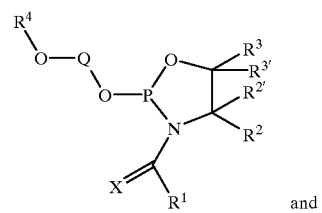

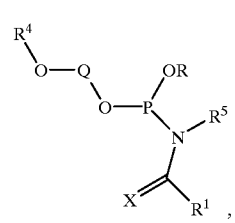

wherein R, $R^1$, X, $R^2$, $R^{2'}$, $R^3$, $R^{3'}$, $R^4$, $R^{15}$, $Q^1$, Q and n are as defined above group consisting of $OR^7$, CN, $NO_2$, $N_3$, and a halogen, wherein $R^7$ is an alkyl, an aryl, or an aralkyl and wherein $R^7$ is unsubstituted or is substituted with one or more halogen atoms.

The N-acylphosphoramidites provide for the stereospecific substitution of tricoordinated phosphorus compounds under basic conditions. In this regard, the monomeric compounds of formulae (I) and (II), and the oligomeric compounds of formula (III), are useful in the synthesis of polymers, particularly oligonucleotide polymers, bearing thermolabile protecting groups on the internucleosidic phosphorus linkage.

Preferably, the N-acylphosphoramidites are hydroxyl-protected monomer-O-(O-protected)-(N-acyl)phosphoramidites, or hydroxyl protected oligomer/polymer-O-(O-protected)-(N-acyl)phosphoramidites, exemplified by formulae (I)-(III). In a preferred embodiment, the compound is a hydroxyl-protected monomer-O-(N-acyl)-1,3,2-substituted oxazaphospholane (formula (I)), which can be isolated as the Rp or Sp chiral form, to be used in the synthesis of polymers containing stereogenic phosphorus centers of predetermined configuration in a site-specific manner.

With respect to the N-acylphosphoramidites, any suitable N-acyl moiety can be used. Suitable acyl moieties include $R^1(C=X)N$—groups which render the phosphorus-(N-acyl) bond sufficiently reactive to allow displacement of the N-acyl group by a nucleophile, preferably under basic conditions. The C=X bond of the N-acylphosphoramidites includes carbonyl and carbonyl equivalents. Thus, the N-acyl group includes carbonyl (wherein X is O) and thiocarbonyl (wherein X is S). Typically, the N-acyl group is a carbonyl, wherein X is O.

The Q in the N-acylphosphoramidites of formulae (I) and (II), and the Q and $Q^1$ in the intermediates obtained therefrom (formula (III)), include nucleosides (natural and modified) and oligomers which include one or more of such nucleosides, as described herein. Any suitable monomer-monomer, monomer-oligomer, oligomer-monomer, or oligomer-oligomer coupling reaction can be accomplished, stereospecifically, using the compounds and methods of the present invention. For example, the N-acylphosphoramidite of formula (I) or (II) can be used to stereospecifically couple a suitably protected nucleoside (or even a suitably protected oligonucleotide) to an oligonucleotide. Thus, the N-acylphosphoramidites described herein can be attached to an oligomer such as, for example, an oligonucleotide (i.e., wherein Q is an oligonucleotide), as well as a monomer (i.e., wherein Q is a nucleoside). The nucleophile which is coupled to the N-acylphosphoramidite also can be monomeric or oligomeric. Accordingly, $Q^1$ also includes oligomers that contain, as a component thereof, a nucleoside substituent as described herein.

In a preferred embodiment, Q and/or $Q^1$ is a nucleoside substituent of the formula:

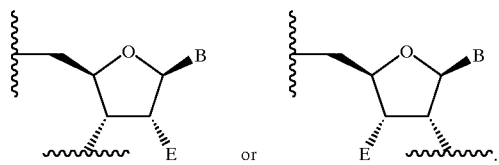

or

In this embodiment, $R^4$ is advantageously a solid support or a protecting group. The protecting group is most preferably a 4,4'-dimethoxytrityl protecting group.

Examples of monomeric N-acylphosphoramidites that can be used in accordance with the present invention include compounds of the formulae:

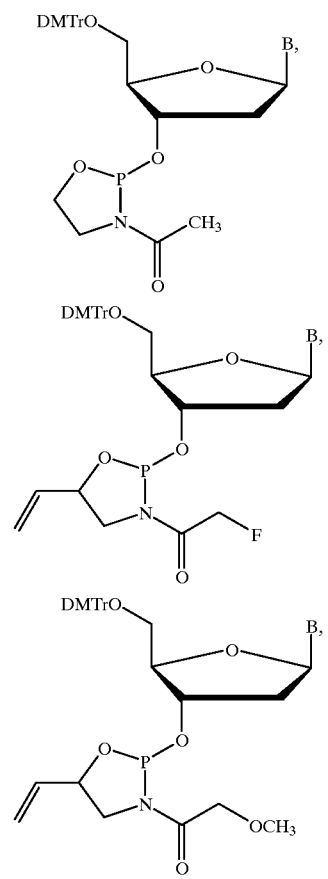

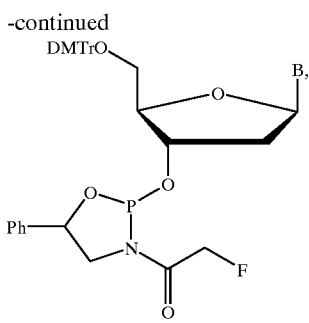

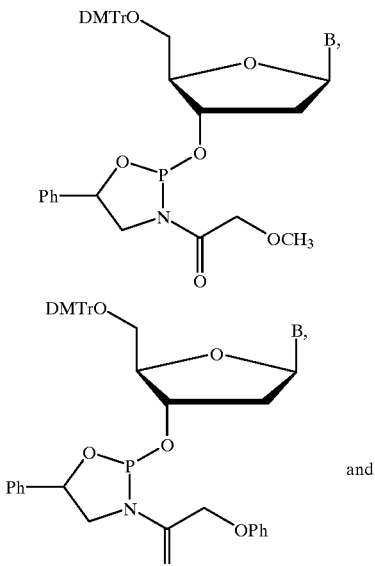

and

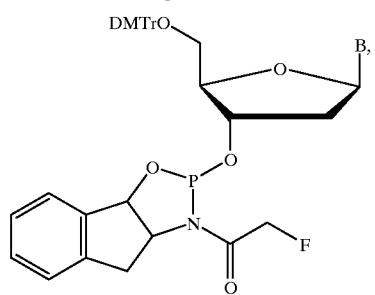

wherein B is as defined above.

Stereospecific coupling reactions can be carried out successively "n" times, for example, starting with a nucleophile $R^4$—O—$Q^1$—OH (wherein $R^4$ and $Q^1$ are as defined above), and continuing thereafter, to provide an intermediate of formula (III), wherein n is an integer from 1 to about 300. It will be appreciated that, when a compound of formula (I) is reacted with a nucleophile $R^4$—O—$Q^1$—OH, "$R^4$" of formula (I) is represented by "$R^{15}$" of formula (III). When the protecting group $R^{15}$ is removed, then $R^{15}$ becomes a hydrogen. $R^4$ and $R^{15}$ desirably are not both solid supports in formula (III). When $R^{15}$ is hydrogen, then another coupling reaction can be carried out, and the process repeated successively, until a polymer of desired length or structure is obtained. In each successive reaction, the Q substituent of formula (I) can be can be independently selected, as desired to obtain a variety of different combinations. As such, Q can be the same or different in each of the units defined by n, when n is greater than 1. In other words, Q is independently selected when n is greater than one. Preferably, n is in the range of from about 3 to about 200; more preferably, n is in the range from about 10 to about 40; and most preferably n is in the range from about 15 to about 25.

Typically, the monomeric units in the polymers prepared in accordance with the present invention are connected via phosphorus diester linkages, for example, phosphate or chiral phosphate (P-chiral) linkages, as desired. However, the compounds and methods of the present invention are not limited to the synthesis of polymers having only phosphorus-linked monomeric units. For example, the compounds of the present invention also can be used to introduce one or more phosphorus-linked units into a polymer having another type of linkage in the structure thereof, for example, a carbonate, a urea, an ester, an ether, or any suitable combination thereof.

Preferred N-acylphosphoramidites include N-acylphosphoramidites of the formula:

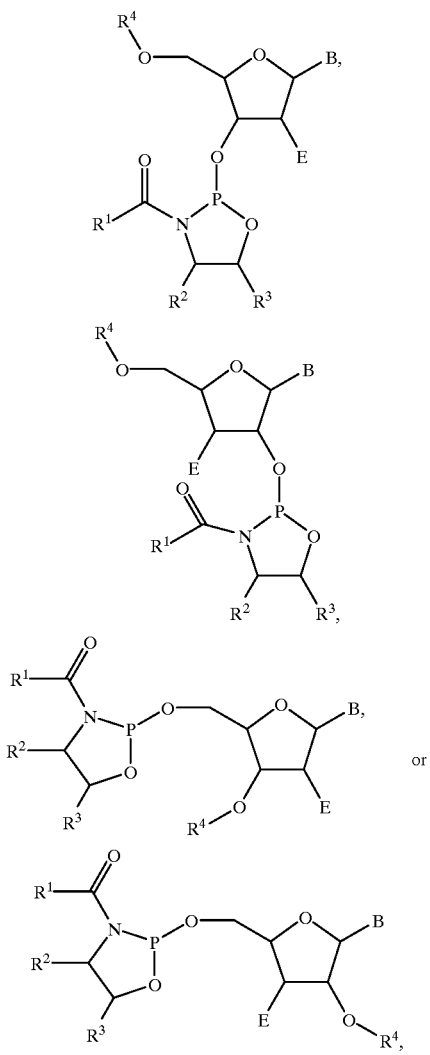

wherein $R^1$–$R^4$, B, and E are as defined above.

As indicated above, particular substituents for $R^1$–$R^3$ can be selected which facilitate thermal cleavage of the protecting group on the non-bridging phosphate or phosphorothioate oxygen after coupling has been carried out.

Generally, oligonucleotide synthesis using an N-acylphosphoramidite can be carried out by the steps of:
(a') reacting a nucleophile that can displace the N-acyl group of an N-acylphosphoramidite of formula (I) or (II), wherein $R^4$ is a protecting group with an N-acylphosphoramidite of formula (I) or (II), preferably in the presence of a base, to produce an adduct of the N-acylphosphoramidite and the nucleophile, the adduct comprising a tricoordinated phosphorus atom;
(b') reacting the adduct with a reagent selected from the group consisting of oxidizing agents, sulfurizing agents, and selenizing agents to produce a product, wherein the tricoordinated phosphorus atom is converted into a phosphorus atom with a valence of greater than three (e.g., a tetracoordinated phosphorus atom);
(c') removing the protecting group $R^4$ from the product;
(d') optionally repeating steps (a') through (c'), one or more times as necessary, until a polymer of specified length is obtained; and
(e') thermally cleaving the bond linking the resulting protecting group bonded to the non-bridging phosphate, phosphorothioate or phosphoroselenoate oxygen atom after step (a'), (b'), (c') or (d'). While the thermal deprotection can be carried out at any stage after any of steps (a')–(d'), it is preferably carried out after step (c') or (d').

Preferably, the N-acylphosphoramidite is a P-chiral N-acylphosphoramidite. When a P-chiral N-acylphosphoramidite is used, the resulting adduct also is P-chiral, since the coupling reaction (step (a')) occurs with stereo specificity. Moreover, reaction of the resulting adduct of step (a') with an oxidizing, a sulfurizing, or a selenizing agent (step (b')) occurs stereospecifically, that is, without any epimerization at phosphorus. For example, sulfurization of the P-diastereomerically pure adduct of step (a'), obtained by using a P-diastereomerically pure N-acylphosphoramidite, results in a P-diastereomerically pure adduct. Although sulfurization reactions are applied to adducts prepared from standard phosphoramidite coupling chemistry, the phosphorothioate products obtained thereby contain a mixture of phosphorus stereoisomers (i.e., they are not stereopure) because the phosphorus adducts prepared via standard phosphoramidite chemistry contain a mixture of stereoisomers. As indicated above, standard phosphoramidite coupling reactions are not stereospecific. Thus, P-chiral coupling adducts can be stereospecifically produced using the N-acylphosphoramidites described herein and, thus, can provide access to oligonucleotides which are stereochemically pure at phosphorus (e.g., oligonucleotide phosphorothioates).

Any suitable base can be used in coupling step (a') including, for example, inorganic and organic bases. Preferably, the base used in step (a') is a relatively non-nucleophilic base, which is more preferably a relatively non-nucleophilic amine base such as, for example, tetramethylguanidine (TMG). Advantageously, and preferably, the coupling is carried out under basic conditions. As a result, the use of an acid in the coupling reaction is avoided, and the P-diastereomerically pure adduct formed in step (a') does not epimerize. Since the coupling reaction of step (a') occurs with complete stereospecificity, the stereochemical purity with respect to phosphorus can be governed by the stereochemical purity of the N-acylphosphoramidite used therein.

Desirably, the N-acylphosphoramidite approach described herein further includes the step of capping the unreacted nucleophilic group after step (b') or (c'). Capping is usually done as a prophylactic measure to prevent the unreacted nucleophilic groups, left over from prior condensation reactions, from reacting in subsequent condensation cycles. Capping promotes synthetic advantages such as, for example, preventing the formation of undesirable side products. When the nucleophile (or oligomeric adduct, if steps (a')–(c') are repeated at least once) is a sugar hydroxyl, capping typically involves acylation of the unreacted sugar hydroxyls.

Typically, the reaction in step (a') leads to formation of a tricoordinated P-chiral product, thereby enabling, in step (b'), the formation of a P-chiral product. Deprotection of the preferred tetracoordinated P-chiral products can provide a P-chiral polymer of predetermined chirality and length. Preferably, the nucleophile is a nucleoside, an oligonucleotide, or a derivative thereof, step (a') utilizes a P-chiral N-acylphosphoramidite, and step (b') comprises sulfurization. Repeating the steps (a')–(c') can be continued as many times as desired, until a polymer of a particular length and chirality is obtained.

As discussed above, formation of a tricoordinated P-chiral product in step (a') can be achieved by using any suitable P-chiral N-acylphosphoramidite, most preferably a P-chiral analog of compound (I) or (II). In accordance with the present invention, P-chiral N-acylphosphoramidites can be obtained by any suitable method such as, for example, chiral synthesis, chromatographic resolution, or any suitable combination thereof. Chromatographic separation of a mixture of P-chiral isomers can be facilitated, for example, if the monomeric subunit of the N-acylphosphoramidite is a chiral molecule, as illustrated, for example, in Scheme 2.

moisture under standard (acidic) conditions which are required to accomplish a coupling reaction. As such, acid-promoted phosphoramidite nucleoside couplings typically are carried out in a moisture-free environment, particularly if the target polymer comprises a large number of monomeric units. Since the N-acylphosphoramidites described herein undergo hydrolytic degradation sluggishly, or not at all, under the coupling conditions of step (a'), the problem of competitive hydrolytic cleavage has essentially been eliminated. As such, the utilization of N-acylphosphoramidites as described herein does not require a scrupulously water-free environment.

In a preferred embodiment, the nucleophile coupled to the N-acylphosphoramidite is attached to a solid support. When the nucleophile is attached to a solid support, the nucleophile is preferably a compound of the formula:

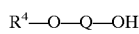

wherein Q is a nucleoside, an oligonucleotide comprising a nucleoside, or an oligomer comprising a nucleoside, wherein the nucleoside is of the formula:

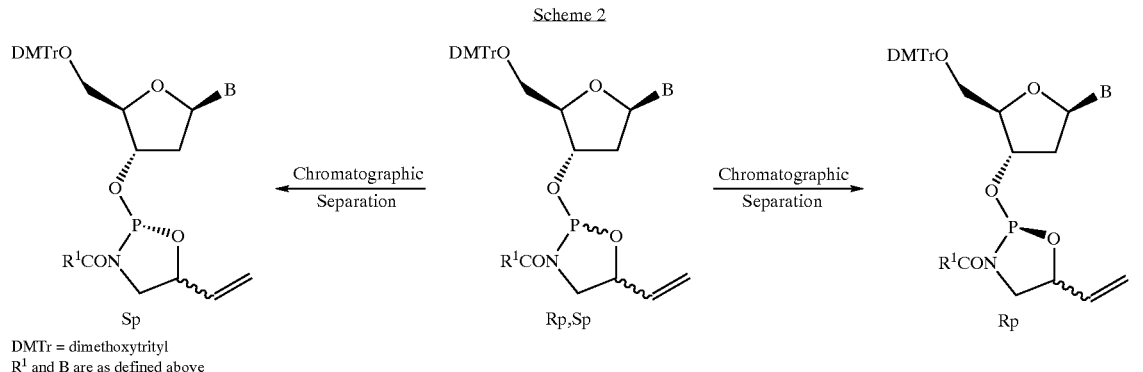

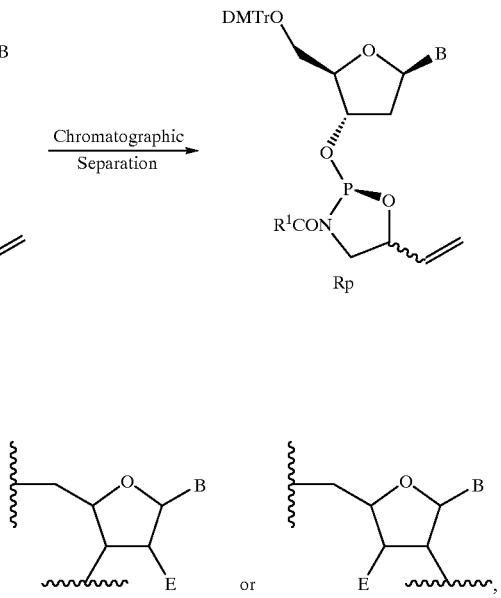

wherein B and E are as defined herein, or an oligomer which includes one of these nucleosides as a component thereof, and $R^4$ is the solid support.

Using this technique, P-chiral products having any desired phosphorus stereochemistries can be stereospecifically prepared simply by selecting the appropriate P-chiral N-acylphosphoramidite and using it in accordance with the method of the present invention. When P-chiral phosphate analogue linkages are desired, the N-acylphosphoramidite approach described herein makes it possible to prepare polymers having a predetermined sequence of P-chirality along the polymer backbone. P-chiral oligonucleotides derived from N-acylphosphoramidites can be employed as hybridization probes, therapeutic agents, e.g., selective protein expression inhibitors, and the like.

There are other advantages to using N-acylphosphoramidite precursors, such as, for example, moisture stability. In particular, the N-acylphosphoramidites described herein are far more stable to moisture under the coupling conditions of step (a') than are the conventional phosphoramidite synthons for which mild acid conditions are required. Moisture instability is one disadvantage inherent in oligonucleotide synthesis using standard phosphoramidite chemistry. In particular, standard phosphoramidite precursors can hydrolytically degrade upon contact with Desirably, the nucleophile is a monomer. In a preferred embodiment, the nucleophile is a monomer and is attached to a solid phase support through a linking group that will resist cleavage in the presence of a base, for example, a base used in step (a'), thereby allowing the resulting oligomer/polymer to remain attached to the solid support throughout each successive coupling step. When a solid support is used in connection with a nucleophile (e.g., a nucleophilic monomer), Q is preferably a nucleoside of the formula:

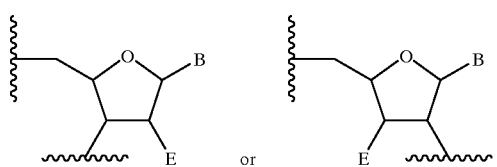

wherein B and E are as defined above. In one preferred embodiment, Q is a nucleoside substituent having a defined stereochemistry, and is represented by the formula:

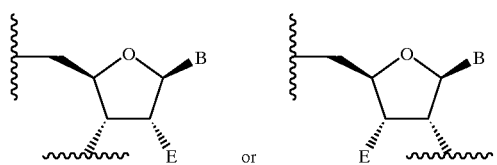

wherein B and E are as defined above.

In a particularly preferred embodiment, a cyclic N-acylphosphoramidite of formula (I) is used to effect the desired coupling, and is represented by the formula:

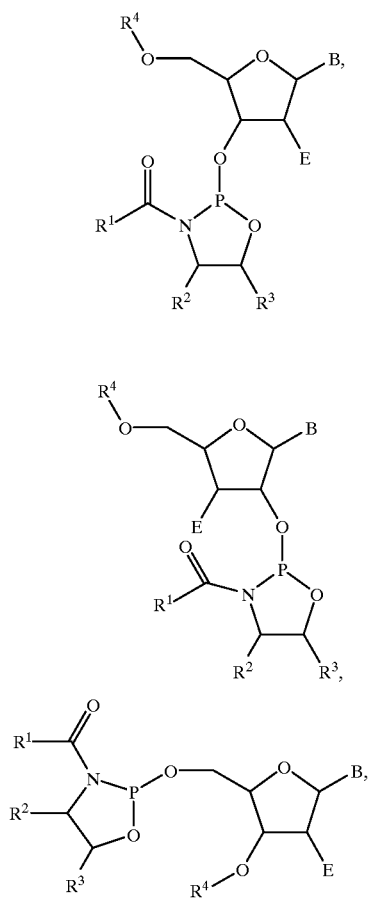

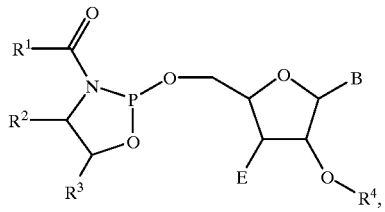

-continued wherein $R^1$–$R^4$, B, and E are as defined above. Preferably, B is a purine, a pyrimidine, adenine, guanine, cytosine, uracil, or thymine, wherein B is unsubstituted or substituted with one or more substituents, which are the same or different, selected from the group consisting of a protecting group, $R^{11}$, $OR^{11}$, $NHR^{11}$, $NR^{11}R^{12}$, CN, $NO_2$, $N_3$, and a halogen, wherein $R^{11}$ and $R^{12}$ are as defined herein.

In one embodiment, $R^1$ is an alkyl, which is unsubstituted or substituted with one or more substituents selected from the group consisting of fluorine, $OR^7$ and $SR^7$, wherein $R^7$ is an alkyl or an aryl. For example, $R^1$ can be a $C_1$–$C_6$ alkyl, which is unsubstituted or substituted with one or more fluorine atoms, e.g., a methyl, which is unsubstituted or substituted with one or more fluorine atoms (e.g., fluoromethyl). In another embodiment, $R^2$, $R^{2'}$, $R^3$, or $R^{3'}$ is a vinyl group, a phenyl or a benzyl. A preferred protecting group for $R^4$ is the 4,4'-dimethoxytrityl group.

Oxidizing agents that can be used in accordance with the present invention include any suitable reagent that can oxidize a tricoordinated phosphorus atom, particularly a phosphite, to provide a phosphorus atom having a valence of higher than three, preferably a tetracoordinated phosphorus atom such as, for example, a phosphate, or an equivalent thereof. Suitable oxidizing agents include, for example, $I_2/H_2O$, peroxides, such as tert-butylhydroperoxide, and the like.

Sulfurizing agents that can be used in accordance with the present invention include any suitable reagent that can sulfurize a tricoordinated phosphorus atom, particularly a phosphite, to provide a phosphorus atom with a valence of greater than three, preferably a tetracoordinated phosphorus atom such as, for example, a phosphorothioate, or an equivalent thereof. Suitable sulfurizing agents include, for example, 3H-1,2-benzodithiol-3-one 1,1-dioxide ("Beaucage Reagent"), phenylacetyl disulfide, bis(O,O-diisopropoxyphosphinothioyl) disulfide, and the like.

Selenizing agents that can be used in accordance with the present invention include any suitable reagent that can selenize a tricoordinated phosphorus atom, particularly a phosphite, to provide a phosphorus atom having a valence of greater than three, preferably a tetracoordinated phosphorus atom such as a phosphoroselenoate, or an equivalent thereof. Suitable selenizing agents include, for example, potassium selenocyanate (KSeCN) or elemental selenium.

N-acylphosphoramidites also can be applied toward the synthesis of unmodified oligonucleotides and to the non-stereospecific synthesis of oligonucleotide analogues, for example, by performing the steps of:

(i) providing a nucleophile;
(ii) reacting the nucleophile, in the presence of a mild acid, with a synthon of the formula:

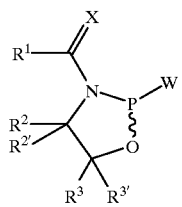

wherein X and $R^1$–$R^{3'}$ are as defined herein, and W is a leaving group amenable to nucleophilic displacement (e.g., a dialkylamino), to produce an adduct of the nucleophile and the synthon, which is an N-acylphosphoramidite having a tricoordinated phosphorus atom;

(iii) reacting, in the presence of a base, the resulting adduct with a nucleoside, having at least one nucleophilic group and at least one suitably protected nucleophilic group, to produce a product;

(iv) oxidatively transforming the tricoordinated phosphorus atom into a tetracoordinated one;

(v) deprotecting the protected nucleophilic group of the resulting product; and (vi) repeating the steps (ii)-(v) until an oligomer or polymer of predetermined length is obtained.

Preferably, this method further comprises the step of capping unreacted nucleophilic groups after step (iii) or (iv), as discussed herein. It is further preferred to attach the first monomer (i.e., the nucleophile in the first coupling reaction of a synthesis) to a solid phase support through a linking group that will resist cleavage, when in the presence of the base used in step (iii).

Preferably, W is displaced by a monomer of the formula $R^4$—O—Q—OH or $R^4$—O—$Q^1$—OH, wherein $R^4$, Q, and $Q^1$ are as defined herein. In a preferred embodiment, W is a dialkylamino having from 2 to about 8 carbon atoms (e.g., dimethylamino, diethylamino, N-methyl-N-isopropylamino, and the like), or a cyclic amine substituent having from 2 to about 6 carbon atoms (e.g., pyrrolidinyl, piperidinyl, morpholinyl, aziridinyl, and the like), wherein one or more carbon atoms of the dialkylamino and cyclic amine substituents are unsubstituted or substituted with one or more heteroatoms, which are the same or different. More preferably W is a dialkylamino, or a cyclic amino. Most preferably, W is a di($C_1$-$C_6$ alkyl)amino (e.g., a diethylamino or a diisopropylamino).

The reactions in step (iii) enable the formation of the tricoordinated P-chiral product and, preferably, step (vi) causes formation of the tetracoordinated P-chiral product in a stereospecific manner. Moreover, thermal deprotection preferably gives either a P-achiral or a P-chiral polymer of predetermined length. In step (iii), suitably protected nucleosides comprise unmodified and/or modified nucleosides. Step (iv) preferably comprises oxidation and/or sulfurization.

When an N-acylphosphoramidite is used, it is preferred that an N-acylphosphoramidite of formula (I) is used. Thus, in a preferred embodiment, the resulting product of steps (a')–(c'), (a')–(d'), (iii), or (iii)-(v) described herein is a compound of formula (III). Compounds of formula (III) are dimeric, when one coupling step is performed (n=1). However, any desired number of subsequent coupling steps can be performed, typically requiring deprotection (step (c) or step (v)) prior to subsequent coupling reactions, wherein each monomeric unit defined by "n" is the same or different, and the substituents $R^1$–$R^4$, $R^{15}$, X, $Q^1$, and Q are as defined herein. Compounds of formula (III) are useful in the synthesis of polymers, particularly phosphodiester-linked polymers, more particularly P-chiral phosphodiester-linked polymers, which can be obtained from (III) via thermal cleavage of the 2-amidoethoxy protecting group bonded to the non-bridging phosphate, phosphorothioate or phosphoroselenoate oxygen atom, as described herein.

Oligomers and polymers synthesized in accordance with the present invention are typically represented by the formula:

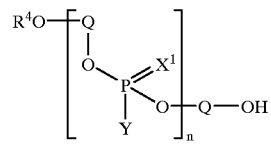

(IIIA)

wherein: Q, $X^1$, and n are as defined above, and Y is any suitable heteroatom or organic substituent, preferably hydroxyl (or a suitable salt thereof). Preferably n is in the range from about 3 to about 200; more preferably, n is in the range from about 10 to about 40; and most preferably in the range from about 15 to about 25. In the polymers synthesized using the methods and compounds of the present invention, Q, $X^1$, and Y, or any combination thereof, can be the same or different when n is 1, and can be the same or different in each of the units defined by n when n is greater than 1.

Typically, $R^4$ is a hydrogen or a hydroxyl protecting group such as, for example, a 4,4'-dimethoxytriphenylmethyl (DMTr), 4-methoxy-triphenylmethyl (MMTr), pixyl, acetyl, 9-fluorenylmethyloxycarbonyl (Fmoc), t-butyldimethylsilyl (TBDMS), and the like. Alternatively, $R^4$ is a reporter group such as, for example, an amine, a mercapto, a phosphate, a phosphorothioate, and the like. Reporter groups preferably contain an active moiety for further reaction with radioactive label such as, for example, $^{32}$P-phosphate, $^{125}$I-iodinated Bolton-Hunter reagent, and the like, or a non-radioactive label such as, for example, fluorescein isothiocyanate (FITC), dansyl chloride, and the like, or any other biologically active group such as, for example, biotin, digoxigenin, and the like. Reporter groups can be introduced by means known to those skilled in the art including, for example, introduction of appropriate linkers, spacers, arms, or other reagents used for manipulating the distance between the reporter group and the polymer.

$X^1$ in formula (IIIA) is preferably S, O, or Se. If desired, $X^1$ also can be a substituted imino of the formula=$NR^{16}$, wherein $R^{16}$ is an alkyl, an aryl, or an alkenyl-substituted aryl substituent. Preferably, Y is an OH (or suitable salt thereof).

In a preferred embodiment, P-chiral polymers that are prepared in accordance with the present invention are of formula (IIIA) above, wherein $X^1$ and Y, or any combination thereof, can be the same or different in any of the units being defined by n. More preferably, P-chiral oligonucleotides prepared in accordance with the present invention are of the formula:

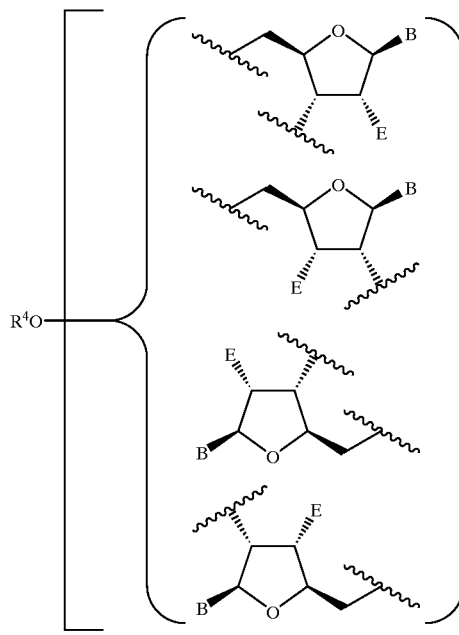 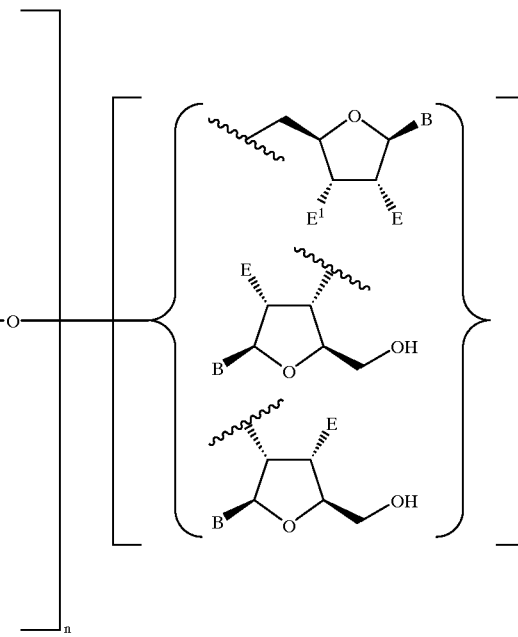

wherein $X^1$, Y, B, E and $R^4$ are as defined herein, and $E^1$ includes the same groups defined herein with respect to E, and E and $E^1$ can be the same or different. B is preferably a natural or a synthetically modified nucleic base, or B is a synthetic analog or reporter group, preferably a reporter group comprising a carboxyl, an alkyl, or an alkylamine. $E^1$ is preferably a 3'-hydroxyl (optionally protected), and E is preferably a hydrogen, a halogen, a hydroxyl, or an appropriately protected hydroxyl, an amine, or an appropriately protected amine, or the like.

A polymer of any suitable length can be prepared in accordance with the method of the present invention. Preferably, n is in the range from about 3 to about 200, but is more preferably in the range from about 12 to about 60. It is understood that the P-chiral oligonucleotides of the invention can include linkages, for example, 5'–3', 5'–2', 5'–5', 3'–3', 2'–2', and 3'14 2' linkages, between nucleosides by the appropriate selection of Q and $Q^1$, as defined herein.

The compounds represented by formulae (I) and (II) are typically prepared from a synthon of the formula:

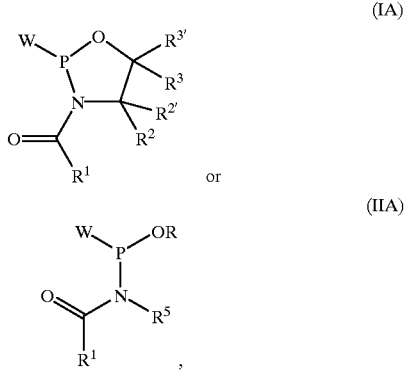

wherein R, $R^1$–$R^3$', and $R^5$ are as defined herein, and W is a leaving group amenable to nucleophilic attack by a free group of the monomer, preferably a monomer of the formula $R^4$—O—Q—OH or $R^4$—O—$Q^1$—OH, wherein $R^4$, Q, and $Q^1$ are as defined herein. Preferably, W is halogen, a dialkylamino having from 2 to about 8 carbon atoms, or a cyclic amine substituent having from 2 to about 6 carbon atoms, wherein at least one carbon of the alkyl groups in the dialkylamino and cyclic amine substituents is optionally substituted with one or more heteroatoms, which are the same or different. More preferably W is a dialkylamino, or a cyclic amino. Most preferably, W is a dialkylamino (e.g., a diethylamino or a diisopropylamino).

EXAMPLES

The following examples further illustrate the invention but, of course, should not be construed as in any way limiting its scope.

Example 1

This example demonstrates the preparation of 2-(N-formyl-N-methyl)aminoethan-1-ol (FIG. 2A).

2-(Methylamino)ethanol (51.0 g, 0.68 mol) was placed in a 250 mL round-bottom flask equipped with a reflux condenser, and cooled to 5° C. by immersion in an ice bath. Ethyl formate (75.0 g, 1.01 mol) was then added, in portions through the condenser to the stirred amino alcohol over a period of 5 min at 5° C. The solution is removed from the ice bath and brought to reflux for 1 h. The solution was then distilled at atmospheric pressure to remove excess ethyl formate, and then carefully distilled under high-vacuum to afford 2-(N-formyl-N-methyl)aminoethan-1-ol as a clear colorless liquid (63.1 g, 0.61 mol, 90%) boiling at 120–122° C. @ 0.15 mm Hg. $^1$H-NMR (300 MHz, DMSO-$d_6$): δ[2.75 (s) and 2.94 (s, 30%) (3H)], 3.27 (m, 2H), 3.47 (m, 3H), [7.94 (s) and 7.99 (s, 30%) (1H)]. $^{13}$C-NMR (75 MHz, DMSO-$d_6$): δ29.2, 34.9, 46.2, 51.2, 57.8, 57.9, 58.1, 58.2, 162.7, 163.0. EI-MS: calcd for $C_4H_9NO_2$ ($M^+$) 103, found 103.

Example 2

This example demonstrates the preparation of N,N,N',N'-tetraisopropyl-O-[2-[(N-formyl-N-methyl)amino]ethyl]phosphordiamidite (compound 120, FIG. 2A).

To an oven-dried 100 mL round-bottom flask containing 50 mL of dry benzene under a dry argon atmosphere, 876 μL of freshly distilled phosphorus trichloride (10 mmol) were added by syringe through a rubber septum. The stirred solution was cooled to 5° C. by immersion in an ice bath and then, 7.7 mL of anhydrous N,N-diisopropylamine (55 mmol) were added by syringe under argon over a period of 30 min. The reaction mixture was removed from the ice bath and allowed to warm to 25° C. under a positive pressure of argon until the formation of bis(N,N-diisopropylamino)chlorophosphine is complete. The rate of the reaction was monitored by $^{31}$P NMR spectroscopy; after ~48 h, the expected chlorophosphine was observed as the major (>96%) reaction product (132.0 ppm downfield relative to a phosphoric acid external standard). 2-(N-Formyl-N-methyl)aminoethan-1-ol (1.03 mL, 10 mmol) was then added to the suspension. The resulting mixture was stirred for 2 h at 25° C. under a positive pressure of argon. $^{31}$P NMR analysis of the reaction mixture indicates that the generation of compound 120 is essentially quantitative (~96%) and reveals two singlets at 118.0 and 118.7 ppm in $C_6D_6$. The suspension was filtered through a sintered glass funnel (coarse porosity, 60 mL) and washed with 20 mL of dry benzene. The filtrates were evaporated under reduced pressure to an oil and dissolved in a minimum amount (~3 mL) of benzene and triethylamine (95:5 v/v). The viscous solution was then applied uniformly to the top of a chromatography column (3×20 cm) packed with a Silica Gel 60 Å (Merck 230–400 mesh, 30 g) slurry in a solution of benzene:triethylamine (95:5 v/v). The column was eluted isocratically with benzene:triethylamine (95:5 v/v) and fractions of 8 mL each were collected. Fractions containing the phosphordiamidite 120 were evaporated to an oil. Residual triethylamine was removed from the product by co-evaporation with toluene (4×10 mL). The phosphordiamidite was then left under high vacuum for at least 3 h. Yield: 2.43 g (7.3 mmol, 73%). $^1$H-NMR (300 MHz, $C_6D_6$): δ[1.14 (d, J=6.9 Hz), 1.16 (d, J=6.7 Hz) 1.18 (d, J=6.7 Hz) (24H)], [2.40 (s, 34%) and 2.64 (s, 66%) (3H)], 2.80 (t, J=5.4 Hz, 2H), 3.43 (m, 4H), [3.29 (dt, J=5.4 Hz, $J_{CP}$=8.5), Hz) and 3.60 (dt, J=5.4 Hz, $J_{HP}$=6.6 Hz)(2H)], [7.82 (s, 34%) and 7.98 (s, 66%) (1H)]. $^{13}$C-NMR (75 MHz, $C_6D_6$): δ24.1, 24.2, 24.6, 24.7, 44.7, 44.9, 45.8 (d, $^2J_{CP}$=8.5 Hz), 50.4 (d, $^2J_{CP}$=8.5 Hz), 61.3, 61.5, 61.9, 62.2, 161.9, 162.3. $^{31}$P-NMR (121 MHz, $C_6D_6$): δ118.0, 118.7. EI-HRMS: calcd for $C_{16}H_{36}N_3O_2P$ ($M^{19+}$) 333.2545, found 333.2528.

Example 3

This example demonstrates the general preparation of 5'-O-(4,4'-dimethoxytrityl)-3'-O-(N,N-diisopropylamino)[2-[(N-formyl-N-methyl)amino]ethoxy]phosphinyl-2'-deoxyribonucleosides.

A suitably protected deoxyribonucleoside (2 mmol) was dried under high vacuum for 2 h in a 50 mL round-bottom flask. Anhydrous acetonitrile (10 mL) was added to the dried nucleoside followed by N,N,N',N'-tetraisopropyl-O-[2-[(N-formyl-N-methyl)amino]ethyl]phosphordiamidite 20 (730 mg, 2.2 mmol). To this solution was added by syringe 4.4 mL of 0.45 M 1H-tetrazole in acetonitrile (2 mmol), dropwise, over a period of 0.5 h. The rates of the reaction were monitored by TLC using benzene:triethylamine (9:1 v/v) as an eluent. Phosphinylation of suitably protected 2'-deoxynucleosides was usually complete within 1 h at 25° C. (for best results, phosphinylation of properly protected 2'-deoxyguanosine is allowed to proceed for 12 h). The reaction mixture was then concentrated under reduced pressure, dissolved in benzene:triethylamine (9:1 v/v), and chromatographed on a silica gel column (4 cm×10 cm) using the same solvent for equilibration and elution. Appropriate fractions were pooled, concentrated, and each of the deoxyribonucleoside phosphoramidites were isolated as a white amorphous powder in yields exceeding 90%. 5'-O-(4,4'-dimethoxytrityl)-3'-O-(N,N-diisopropylamino)[2-[(N-formyl-N-methyl)amino]ethoxy]phosphinyl-deoxythymidine (compound 101, FIG. 2A). $^{31}$P-NMR (121 MHz, $C_6D_6$): δ145.3, 145.2, 145.0, 144.8. FAB-HRMS: calcd for $C_{41}H_{53}N_4O_9P$ $(M+Cs)^+$ 909.2604, found 909.2544. $N^6$-benzoyl-5'-O-(4,4'-dimethoxytrityl)-3'-O-(N,N-diisopropylamino)[2-[(N-formyl-N-methyl)amino]ethoxy]phosphinyl-2' deoxyadenosine. $^{31}$P-NMR (121 MHz, $C_6D_6$): δ145.7, 145.6, 144.9. FAB-HRMS: calcd for $C_{48}H_{56}N_7O_8P$ $(M+Na)^+$ 912.3827, found 912.3843. $N^2$-isobutyryl-5'-O-(4,4'-dimethoxytrityl)-3'-O-(N,N-diisopropylamino)[2-[(N-formyl-N-methyl)amino]ethoxy]phosphinyl-2'deoxyguanosine. $^{31}$P-NMR (121 MHz, $C_6D_6$): δ145.7, 140.9. FAB-HRMS: calcd for $C_{45}H_{58}N_7O_9P$ $(M+Na)^+$ is 894.3933, found 894.3978.

Example 4

This example describes generally the automated synthesis of oligonucleotides using a phosphoramidite precursor.

The automated synthesis of DNA/RNA oligonucleotides is performed on DNA/RNA synthesizers using the corresponding nucleoside phosphoramidites (examples of which are shown in FIG. 1C (compound 101) and FIG. 2B (compounds 102–109)) according to the manufacturers recommendation. A general description of the various steps involved in, for example, solid-phase DNA synthesis is described in Beaucage, *Methods in Molecular Biology*, Vol. 20: *Protocols for Oligonucleotides and Analogs*, (S. Agrawal, ed.), Humana Press: Totowa, N.J., pp. 33–61; Beaucage et al., *Current Protocols in Nucleic Acid Chemistry*, Vol.1 (Beaucage S. L., Bergstrom, D. E., Glick, G. D. Jones R. A. eds), John Wiley and Sons: New York, 2000, pp. 3.3.1–3.3.20; and Beaucage et al., *Tetrahedron*, 48, 2223–2311 (1992), and references therein.

Example 5

This example describes a general procedure for the thermolytic cleavage of phosphate/thiophosphate protecting groups from chemically synthesized oligonucleotides.

Upon completion of solid-phase oligonucleotide synthesis, the solid-phase bound oligonucleotide is 5'-detritylated and then N-deprotected by treatment with, for example, pressurized ammonia gas (10 bar at 25° C.) for at least 10 h. The partially deprotected oligonucleotides is eluted from the column chamber with an aqueous solution of acetonitrile (MeCN, 2 parts) in 0.1 M triethylammonium acetate, pH 7.0 (TEAA, 3 parts). For a typical 0.2 μmol synthesis column, 1 mL of the aqueous MeCN/TEAA solution is sufficient for complete elution of the oligonucleotide. The oligonucleotide solution is then heated at 90° C. up to 3 h in a sealed glass vial to effect the thermolytic cleavage of the phosphate/thiophosphate protecting group. The time required for such a deprotection depends on the nature of the phosphate/thiophosphate protecting group that has been used.

Example 6

Figure 3:
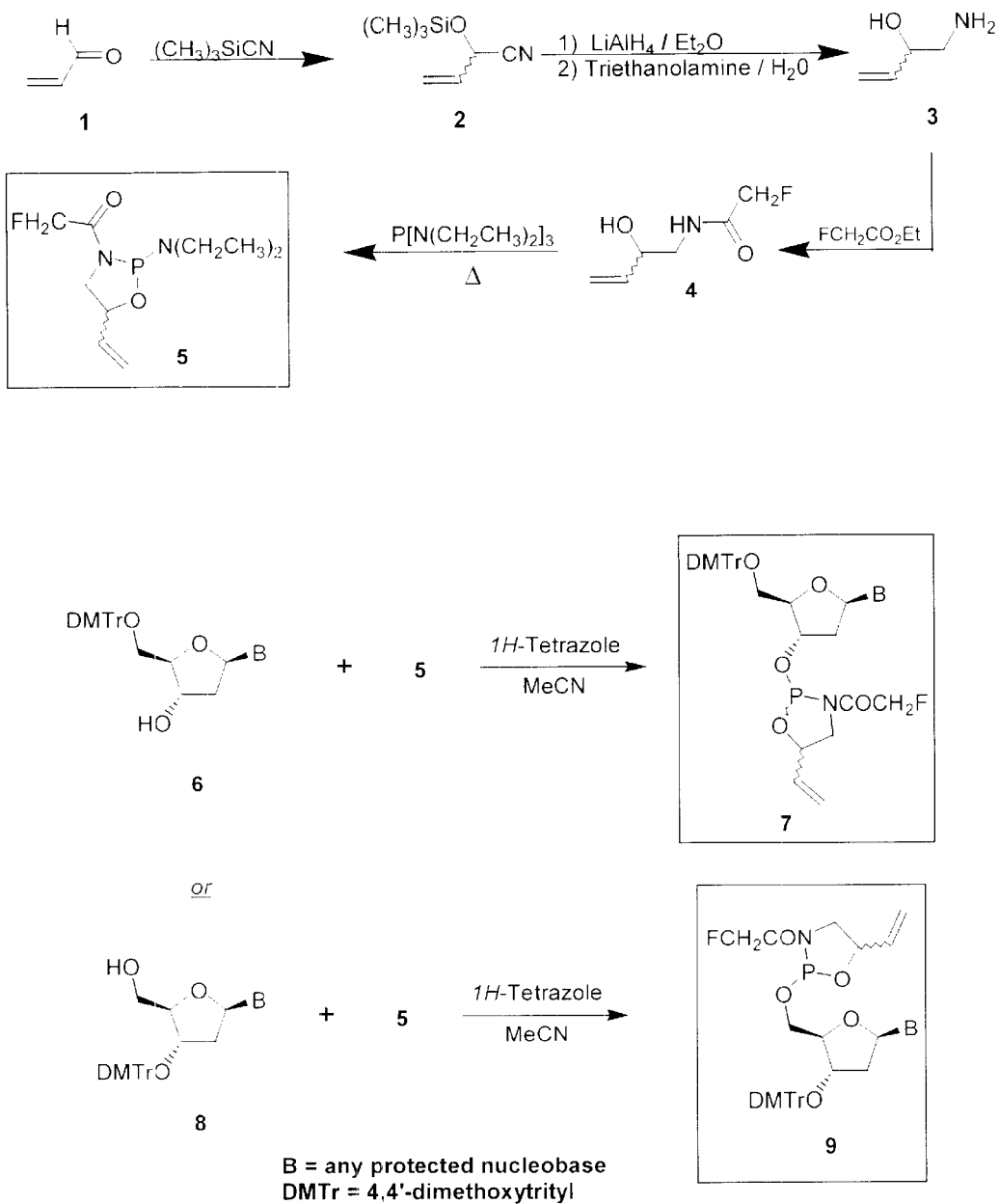
FIG. 3 illustrates the synthesis of various N-acylphosphoramidite of various.

This example illustrates the general synthesis of an N-acylphosphoramidite. The reaction schemes referenced in this example are generally illustrated in FIG. 3.

Typically, the synthon precursor (FIG. 3) is synthesized by first refluxing a mixture of acrolein (1), trimethylsilyl cyanide, and catalytic amounts of zinc iodide according to the procedure reported by Gardrat et al. (*J. Heterocyclic Chem.*, 27, 811 (1990)). Reduction of the resulting nitrile 2 with $LiAlH_4$ in $Et_2O$ afforded amino-alcohol 3. Heating 3 with a slight excess (1.1 molar equiv) of ethyl fluoroacetate at 120° C. until all ethyl alcohol has distilled off gave the hydroxylated amide 4 in 88% yield (b.p. 83–84° C./0.1 torr). An equimolar solution of hexaethylphosphorus triamide and 4 was heated to 120° C. until all diethylamine has distilled off. Vacuum distillation afforded the oxazapholane 5 in 69% yield.

Nucleoside cyclic acylphosphoramidite 7 was prepared by the reaction of a suitably protected nucleoside 6 with equimolar amounts of 5 and 1H-tetrazole in anhydrous dichloromethane for 4 h at ambient temperature. Following evaporation of the reaction mixture, the residue is purified using a short silica gel column chromatography. The nucleosidic synthon 7 is rapidly eluted with a solution of acetonitrile:chloroform (1:2 v/v). Removal of the eluent under reduced pressure afforded 7 as a white foam. The nucleoside cyclic acylphosphoramidite 9 is prepared in a similar manner from nucleoside 8 and compound 5.

Example 7

Figure 4:
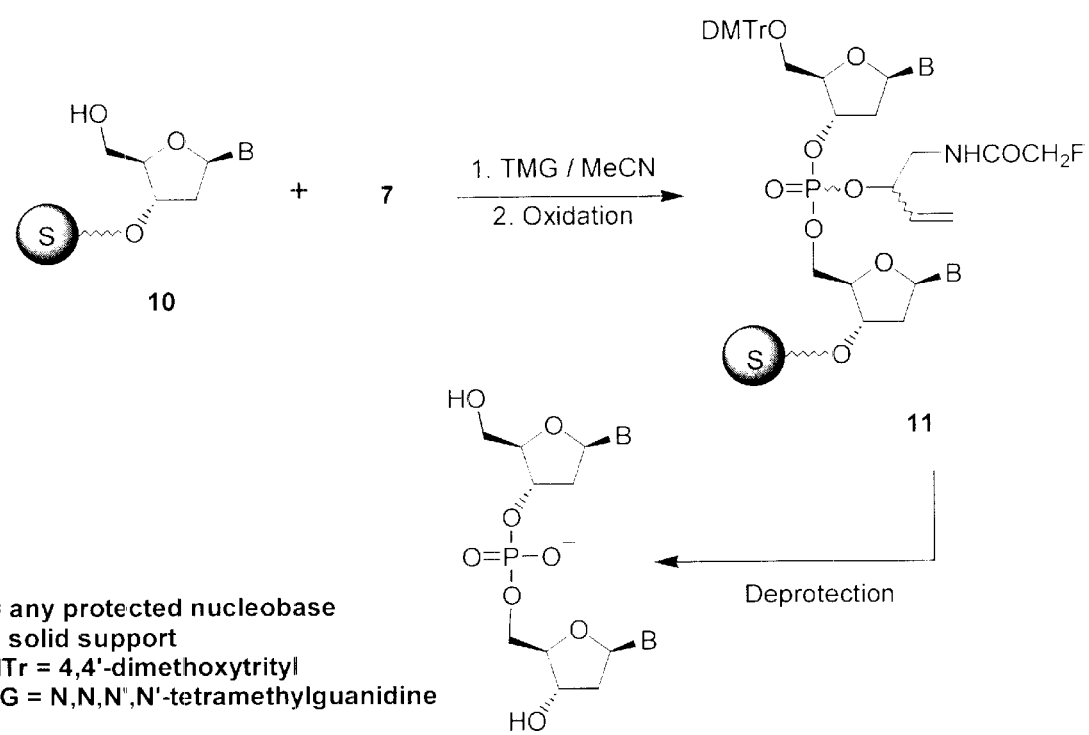
FIG. 4 illustrates the solid phase synthesis of an oligonucleotide using an N-acylphosphoramidite precursor.

This example illustrates a solid phase synthesis using an N-acylphosphoramidite. The general reaction scheme is illustrated in FIG. 4, in which nucleoside cyclic acylphosphoramidite 7 (FIG. 3) is specifically applied to the manual solid-phase synthesis of a decanucleotide ($dC_{10}$). A solid support is denoted in FIGS. 4 and 5 by a darkened sphere with "S" in the center.

Because of the sensitivity of standard succinyl linkers to strong bases, the first nucleoside monomer was attached to long chain alkylamine controlled pore glass (LCAA-CPG) to generate 10 has been modified. The attachment of the leader nucleoside to LCAA-CPG is accomplished via a sarcosine succinyl linkage according to the method of Brown et al. (*J. Chem. Soc. Chem. Commun.*, p. 891–893 (1989)). A column filled with 0.2 mmol of 10, wherein the 5'—OH was protected with a DMTr group, was treated with 2.5 mL of 3% trichloroacetic acid in dichloromethane for 1 min to ensure complete cleavage of the 5'-O-dimethoxytrityl (DMTr) protecting group. The column was then washed with 5 mL of acetonitrile (MeCN) and treated with a solution of 7 (10 mg) in 200 mL of 7.5% N,N,N',N'-tetramethylguanidine (TMG) in MeCN for 3 min. A solution (1 mL) of Cap A and Cap B (1:1) was pushed through the column, left for 1 min, and then washed with MeCN (5 mL), after which a solution of 1 M tert-butylhydroperoxide in dichloromethane (1 mL) was pushed through the column for 1 min, and washed with MeCN (5 mL). This cycle was repeated 8 additional times.

Stepwise DMTr analysis indicated that each coupling yield proceeded with high efficiency, typically 90% or greater. The content of the column is then transferred into a glass vial, and deprotected. The crude oligomer can be characterized by reversed phase (RP) HPLC and polyacrylamide gel electrophoresis (PAGE).

Figure 5:
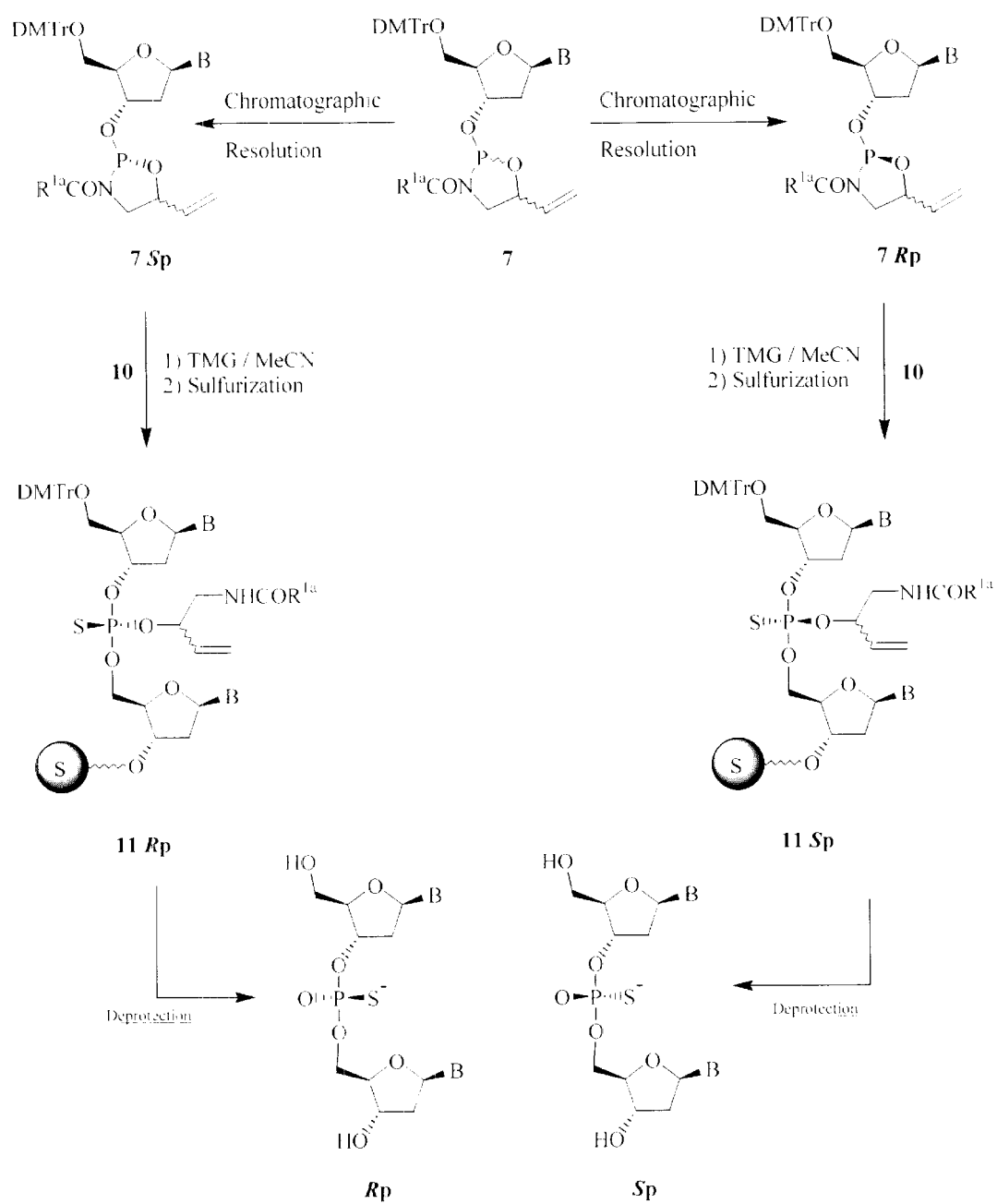
FIG. 5 illustrates the solid phase stereocontrolled synthesis of phosphorothioate oligonucleotides using an N-acylphosphoramidite precursor.

To enable, for example, the synthesis of thioated oligonucleotides stereogenically at phosphorus, the synthon 7 (FIG. 3) must first be separated into its Rp and Sp diastereoisomers (see FIG. 5). This is accomplished by chromatography on functionalized silica (C-1, C-2, C-4, C-8, or C-18 reversed-phase silica).

Example 8

This example illustrates the application of the synthetic cycle described in Example 7, in the stereospecific synthesis of oligonucleotide phosphorothioates. The reaction scheme is illustrated generally in FIG. 5.

A diastereomeric mixture of nucleosidic N-acylphosphoramidite 7 was chromatographically separated into its Rp and Sp isomers, 7Rp and 7Sp, respectively. Each P-chiral isomer was coupled with nucleophilic monomer 10 (FIG. 4), using the conditions of Example 7, to provide P-chiral adducts. The coupling reactions are stereospecific. Sulfurization of the resulting adducts results in the formation of the 11Sp and 11Rp isomers, as illustrated in FIG. 5. Deprotection of the solid support and the 2-amidoethoxy fragment from the sulfurized products is therefore expected to provide stereochemically pure Rp and Sp oligonucleotide products.

It should be noted that the oxidant in the oxidation step is replaced by a sulfur-transfer reagent such as 3H-1,2-benzodithiol-3-one 1,1-dioxide, phenylacetyl disulfide, bis (O,O-diisopropoxyphosphinothioyl) disulfide, and the like. In order to ensure optimum sulfurization, a capping step should be performed after the sulfur transfer step.

Example 9

This example illustrates the preparation of various nucleosidic N-acylphosphoramidites, wherein the N-acyloxazaphospholane moiety is introduced at different hydroxyls of a differentially protected nucleoside core. The reaction schemes are illustrated generally in FIG. 6.

Using the procedure of Example 6, nucleophilic monomers 12, 14, 16, and 18 were coupled to synthon 5 using tetrazole, to provide nucleosidic N-acylphosphoramidites 13, 15, 17, and 19, respectively. The resulting nucleosidic N-acylphosphoramidites can be used as a vehicle for one or more coupling reactions, to provide oligomer or polymer products. Alternatively, the resulting nucleosidic N-acylphosphoramidites can be separated into their Rp and Sp isomers prior to their use as coupling reagents. The phospholane moiety of nucleosidic N-acylphosphoramidites 13, 15, 17, and 19 are attached to either the 3'- or 5'-hydroxyl in the case of 2'-deoxyribonucleosides or, additionally, to the 2'-hydroxyl in the case of ribonucleosides. These products also represent various ribonucleoside monomers that can be used for solid-phase synthesis (both stereospecific and non-stereospecific) of oligoribonucleotides and their analogues as illustrated in FIG. 4 and FIG. 5.

Example 10

This example illustrates the preparation of acyclic N-acylphosphoramidites. The nucleoside acylphosphoramidites can be applied in a manner similar to that described in Examples 7 and 8, and FIGS. 4–5. The reaction scheme is illustrated generally in FIG. 7. A solid support is denoted in FIG. 7 by a darkened sphere with "S" in the center.

Figure 7:
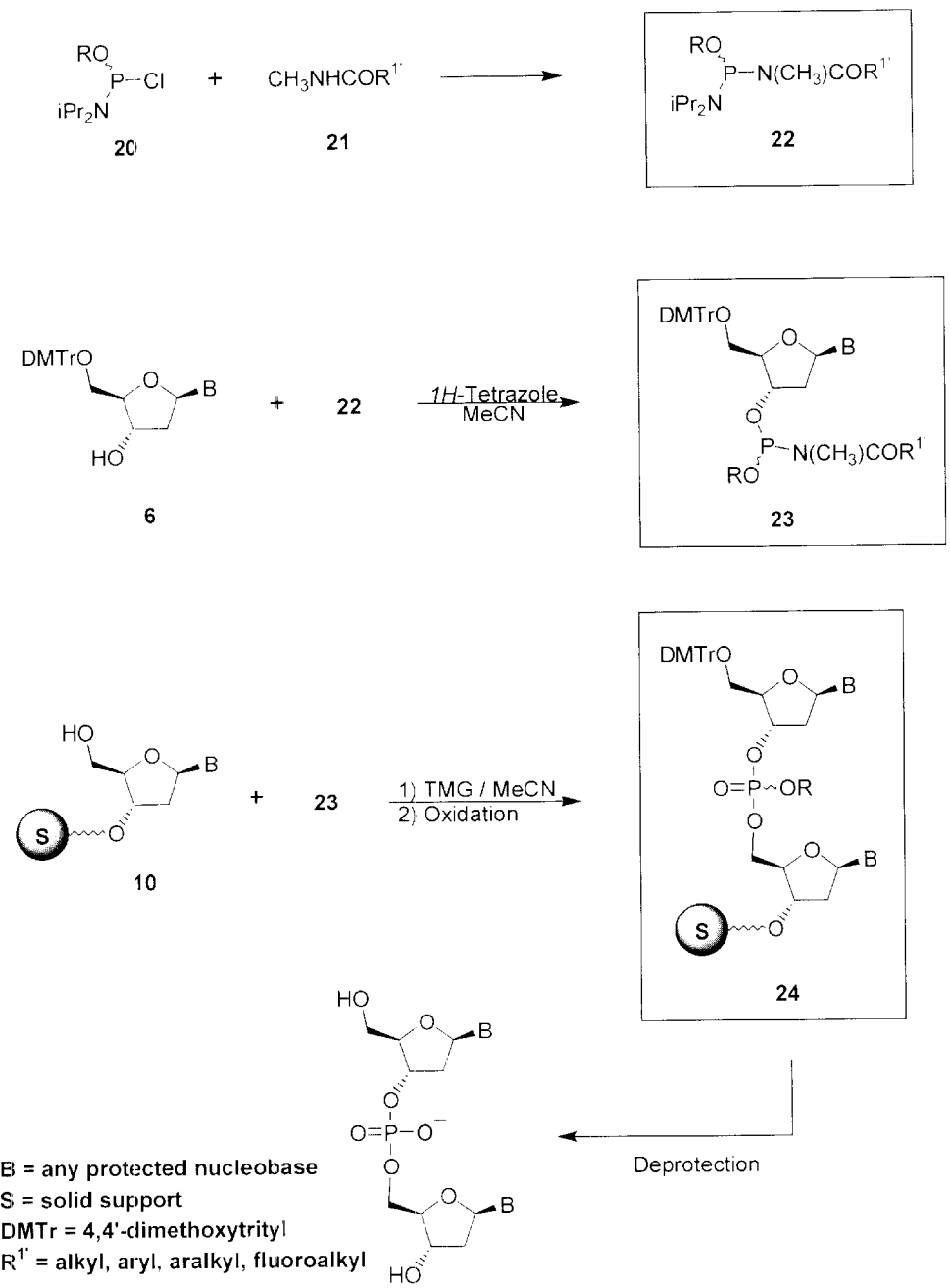
FIG. 7 illustrates the preparation of acyclic N-acylphosphoramidites and their application in solid phase synthesis.

As illustrated in FIG. 7, the non-nucleosidic chlorophosphoramidite derivative 20 is condensed with a suitable N-methylamide (21) to generate the acylphosphoramidite 22. Reaction of 22 with suitably protected nucleosides 6 (FIG. 3) in the presence of 1H-tetrazole affords the corresponding nucleoside 3'-acylphosphoramidites 23 as a mixture of P-diastereoisomers. These amidites are activated under basic conditions and are expected to be useful in solid-phase oligonucleotide synthesis in a manner similar to that shown in FIG. 4. Nucleoside 5'-acylphosphoramidites similar to 9 (FIG. 3) also can be applied for the same purpose. Alternatively, separation of the Rp- and Sp-diastereoisomers of 23 are expected to enable the stereospecic synthesis of thioated oligonucleotides in a manner similar to that illustrated in FIG. 5. In this context, ribonucleoside acylphosphoramidites of formula

Figure 6:
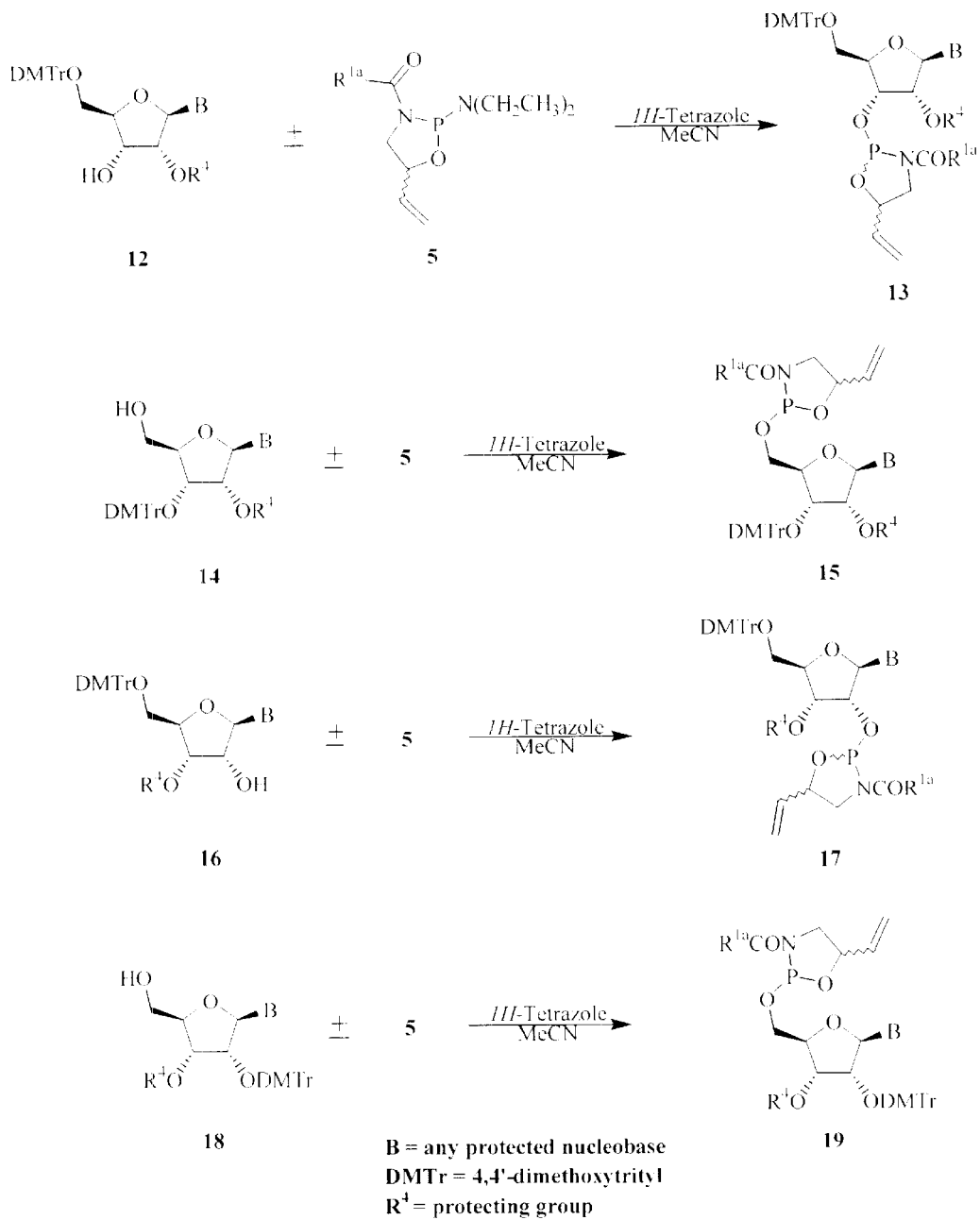
FIG. 6 illustrates the synthesis of various N-acylphosphoramidites.

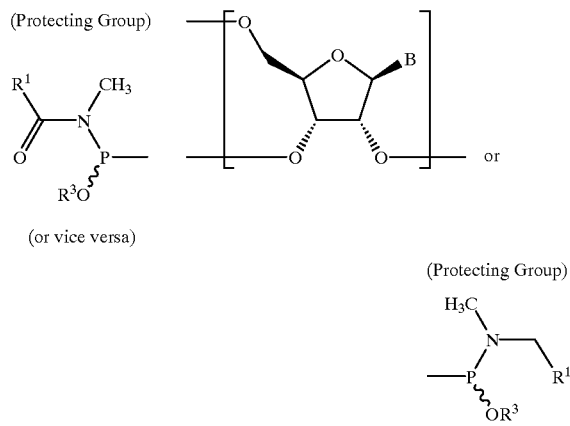

can be used in accordance with the present invention for ribonucleotide syntheses, and are expected to work in the same manner as the cyclic species, for example, 13, 15, 17, and 19 (FIG. 6).

Example 11

Figure 8:
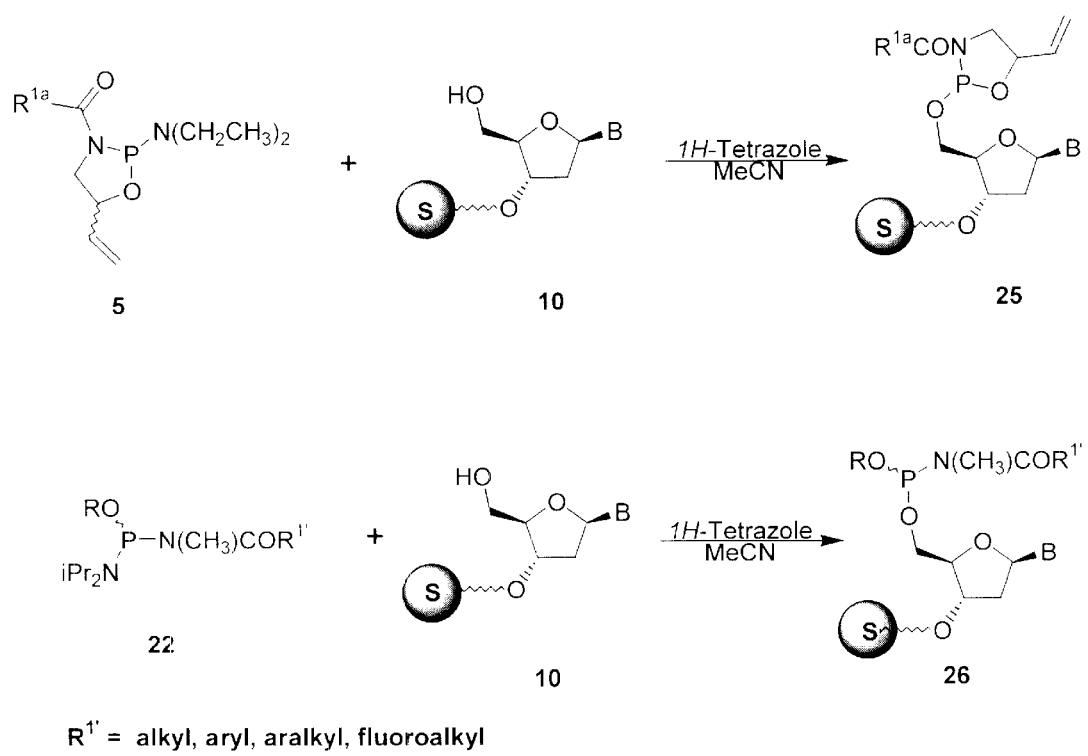
FIG. 8 illustrates the preparation of cyclic and acyclic N-acylphosphoramidites.
Figure 9:
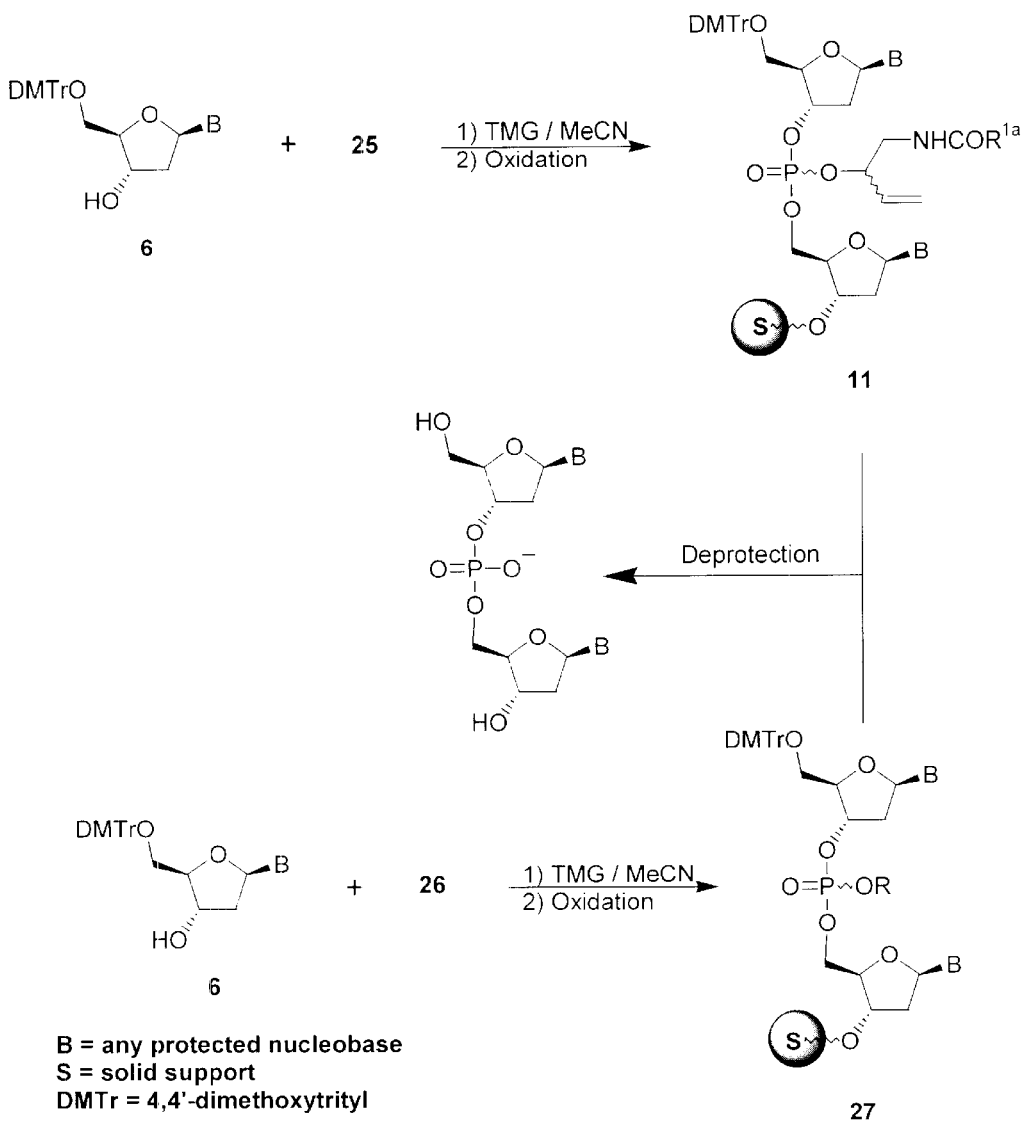
FIG. 9 illustrates the preparation of an oligonucleotide using either cyclic or acyclic N-acylphosphoramidite precursors.

This example demonstrates an alternate approach to the synthesis of oligonucleotides via nucleoside cyclic acylphosphoramidites and acylphosphoramidites, as illustrated in FIGS. 8 and 9. A solid support is denoted in FIGS. 8 and 9 by a darkened sphere with "S" in the center. The strategy was demonstrated by reacting non-nucleosidic cyclic N-acylphosphoramidite 5 (FIG. 3) and acylphosphoramidite 22 (FIG. 7) with the functionalized solid-support-bound 10 (FIG. 4) in the presence of 1H-tetrazole to generate 25 and 26, respectively, as shown in FIG. 8. The reaction of suitably protected nucleoside 6 with 25, or 6 with 26, under basic conditions, followed by oxidation, provided dinucleotides 11 and 27, respectively. Deprotection of 11 and 27 provides the same dinucleotide, as shown in FIG. 9. The same strategy applies with respect to the synthesis of ribonucleotide and the non-stereospecific synthesis of thioated oligonucleotides. The solid-phase synthesis of a decanucleotide ($dC_{10}$) has been achieved using a DNA synthesizer.

General Protocol for Examples 12–17

For the synthesis of oligonucleotides using 5'-O-dimethoxytrityl-3'-O-(5-phenyl-3-N-fluoroacetyl)-1,3,2-oxazaphospholanyl-2'-O-deoxyribonucleoside derivatives in examples 12–17, the general protocol is as follows. The syntheses were performed in a standard DNA synthesis column as available from many suppliers. Standard LCAA-CPG from Applied Biosystems (Masterpiece) columns are used.

The syntheses were carried out by way of the following general steps. The steps were not necessarily done in numerical order within a particular synthesis cycle. The particular sequence of steps used is indicated separately in each example.

In step 1, the appropriate CPG-bound nucleoside is detritylated in accordance with a standard procedure.

In step 2, 5'-O-Dimethoxytrityl-3'-O-(5-phenyl-3-N-fluoroacetyl)-1,3,2-oxazaphospholanyl-2'-O-deoxyribonucleoside derivatives (5 mg, ca. 5 µmol) are dissolved in acetonitrile (200 µL). Tetramethylguanidine (TMG, 4 µl, ca. 30 µmol) is subsequently added and the mixture is applied to the synthesis column.

In step 3, a standard oxidation or sulfurization reaction is carried out after the reaction of step 2 is continued for 5 min.

Steps 2 and 3 are repeated to optimize the yield for a particular synthesis cycle. Steps 2 and 3 need not be performed more than once for a particular synthesis cycle. However, yields are typically improved (e.g., resulting in nearly 100% overall yield) if steps 2 and 3 are repeated within a particular synthesis cycle. Optionally, steps 2 and 3 can be repeated three or more times, as desired, to optimize the yield for a particular synthesis cycle even further.

In step 4, the synthesis cycle is concluded with a capping step. Synthesis cycles can be repeated until the designed sequence length is obtained.

In step 5, the synthetic oligonucleotide is subjected to post-synthesis cleavage from the support, and deprotection.

Example 12

This example describes the synthesis of a dinucleotide using an N-acylphosphoramidite, particularly $T_{PO}T$. The following steps were used in the present example.

Step 1: The bound nucleoside was treated with 3% trichloroacetic acid/dichloromethane (Applied Biosystems DNA synthesis reagent (3 mL, 1 min)), followed by washing with acetonitrile (3 mL, 30 s).

Step 2: 5'-O-Dimethoxytrityl-3'-O-(5-phenyl-3-N-fluoroacetyl)-1,3,2-oxazaphospholanyl-2'-O-deoxythymidine (5 mg, ca. 5 µmol) and tetramethylguanidine (TMG, 4 µl, ca. 30 µmol) in acetonitrile (200 µl) were added to the column and reacted for 5 min., followed by washing with acetonitrile (3 mL, 30 s).

Step 3: The resulting product was treated with iodine/water/pyridine/tetrahydrofuran (Applied Biosystems DNA synthesis reagent), (500 µl, 30 s), followed by washing with acetonitrile (3 mL, 30 s).

Step 5: The dinucleotide can be cleaved from the support and deprotected.

In the present example, a standard column DMT-T-LCAA-CPG (0.2 µmol) can be used and subjected to the above steps in the following sequence:

1, 2, 3, 2, 3, 1, 5.

Example 13

This example describes the synthesis of P-diasteriomerically pure phosphorothioate [Rp]-$C_{PS}C$. The following steps were used in the present example.

Step 1: The bound nucleoside was treated with 3% trichloroacetic acid/dichloromethane (Applied Biosystems DNA synthesis reagent), (3 mL, 1 min), followed by washing with acetonitrile (3 mL, 30 s).

Step 2: [Sp]-N4-Benzoyl-5'-O-dimethoxytrityl-3'-O-(5-phenyl-3-N-fluoroacetyl)-1,3,2-oxazaphospholanyl-2'-O-deoxycytidine (5 mg, ca. 5 µmol) and tetramethylguanidine (TMG, 4 µl, ca 30 µmol) in acetonitrile (200 µl) were added to the column and reacted for 5 min, followed by washing with acetonitrile (3 mL, 30 s).

Step 3: The resulting product was treated with 3H-1,2-benzodithiol-3-one 1,1-dioxide (1% Beaucage Reagent in acetonitrile (w/v)), 3 min, followed by washing with acetonitirile (3 mL, 30 s).

Step 5: The dinucleotide can be cleaved from the support and deprotected.

In the present example, a standard column DMT-CBz-LCAA-CPG (0.2 µmol) can be used and subjected to the above steps in the following sequence:

1, 2, 3, 2, 3, 1, 5.

Example 14

This example describes the synthesis of a P-diastereomerically pure phosphorothioate-linked trinucleotide (trimer), [Rp, Rp]$C_{PS}C_{PS}C$. The following steps were used in the present example.

Step 1: The bound nucleoside was treated with 3% trichloroacetic acid/dichloromethane (Applied Biosystems DNA synthesis reagent), (3 mL, 1 min), followed by washing with acetonitirile (3 mL, 30 s).

Figure 10A:
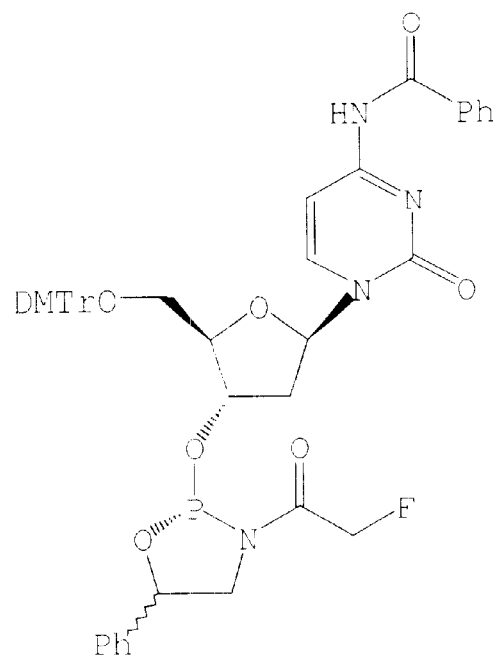
FIG. 10A illustrates the structure of a P-chiral ($S_P$) N-acylphosphoramidite.

Step 2: [Sp]-N4-Benzoyl-5'-O-dimethoxytrityl-3'-O-(5-phenyl-N-fluoroacetyl)-1,3,2-oxazaphospholanyl-2'-O-deoxycytidine (FIG. 10A, 5 mg, ca. 5 µmol) and tetramethylguanidine (TMG, 4 µl, oxazaphospholanyl-2'-O-(5-phenyl-3-N-fluoroacetyl)-1,3,2-oxazaphospholanyl-2'-O-deoxycytidine (5 mg, ca. 5 µmol) and tetramethylguanidine (TMG, 4 µl, ca. 30 µmol) in acetonitrile (200 µl) were added to the column and reacted for 5 min., followed by washing with acetonitrile (3 mL, 30 s).

Step 3: The resulting product from step 2 was treated with 3H-1,2,-benzodithiol-3-one 1,1-dioxide (1% Beaucage Reagent in acetonitrile (w/v)), 3 min, followed by washing with acetonitrile (3 mL, 30 s).

Step 4: The resulting product from step 3 was capped with acetic anhydride/lutidine/tetrahydrofuran (Applied Biosystems DNA synthesis reagent), (1 mL), mixed with 1-methylimidazole/tetrahydrofuran (Applied Biosystems DNA synthesis reagent), (1 mL), 2 min, followed by washing with acetonitrile (3 mL, 30 s).

Step 5: The trinucleotide can be cleaved from the support and deprotected.

In the present example, a standard column DMT-CBz-LCAA-CPG (0.2 µmol) can be used and subjected to the above steps in the following sequence:

1, 2, 3, 2, 3, 4, 1, 2, 3, 2, 3, 5.

The product obtained in accordance with this example can be analyzed by RP-HPLC. The P-diastereomeric purity can be confirmed by co-injection of the trimer prepared in accordance with this example and the corresponding P-diastereomeric mixture obtained by the standard phosphoramidite method.

Example 15

This example describes the synthesis of a P-diastereomerically pure phosphorothioate-linked trinucleotide (trimer), [$S_P$, $S_P$]$C_{PS}C_{PS}C$. The following steps were used in the present example.

Step 1: The bound nucleoside was treated with 3% trichloroacetic acid/dichloromethane (Applied Biosystems DNA synthesis reagent), (3 mL, 1 min), followed by washing with acetonitrile (3 mL, 30 s).

Figure 10B:
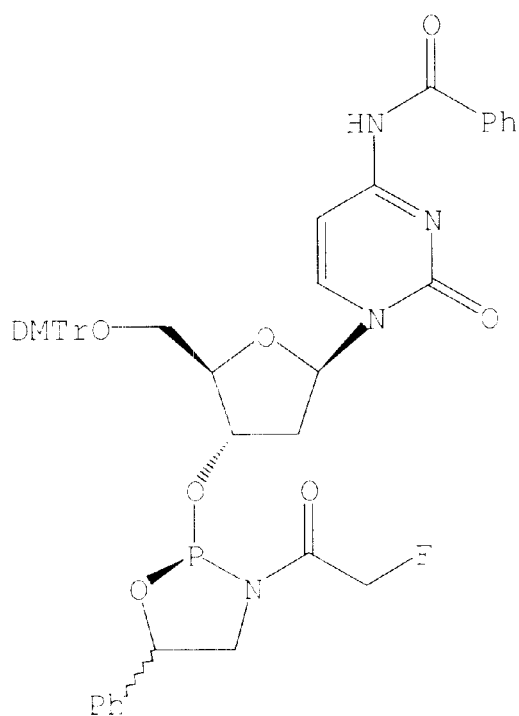
FIG. 10B illustrates the structure of a P-chiral ($R_P$) N-acylphosphoramidite.

Step 2: [Rp]-N4-Benzoyl-5'-O-dimethoxytrityl-3'-O-(5-phenyl-3-N-fluoroacetyl)-1,3,2-oxazaphospholanyl-2'-O-deoxycytidine (FIG. 10B, 5 mg, ca. 5 µmol) and tetramethylguanidine (TMG, 4 µl, ca. 30 µmol) in acetonitrile (200 µl) were added to the column and reacted for 5 min, followed by washing with acetonitrile (3 mL, 30 s).

Step 3: The resulting product from step 2 was treated with 3H-1,2-benzodithiol-3-one 1,1-dioxide (1% Beaucage Reagent in acetonitrile (w/v)), 3 min, followed by washing with acetonitrile (3 mL, 30 s).

Step 4: The resulting product from step 3 was capped with acetic anhydride/lutidine/tetrahydrofuran (Applied Biosystems DNA synthesis reagent), (1 mL), 2 min., followed by washing with acetonitrile (3 mL, 30 s).

Step 5: The trinucleotide can be cleaved from the support and deprotected.

In the present example, a standard column DMT-CBz-LCAA-CPG (0.2 µmol) can be used and subjected to the above steps in the following sequence:

1, 2, 3, 2, 3, 4, 1, 2, 3, 2, 3, 5.

The product obtained in the present example can be analyzed by RP-HPLC. P-diastereomeric purity can be confirmed by co-injection of the trimer prepared in this example and the corresponding P-diastereomeric mixture obtained by the standard phosphoramidite method.

Example 16

This example describes the synthesis of a P-diastereomerically pure phosphorothioate-linked tetramer [Rp, Sp, Rp]-$C_{PS}C_{PS}C_{PS}C$. The following steps were used in the present example.

Step 1: The bound nucleoside was treated with 3% trichloroacetic acid/dichloromethane (Applied Biosystems DNA synthesis reagent), (3 mL, 1 min), followed by washing with acetonitrile (3 mL, 30 s).

Step 2: [Sp]-N4-benzoyl-5'-O-dimethoxytrityl-3'-O-(5-phenyl-3-N-fluoroacetyl)-1,3,2,-oxazaphospholanyl-2'-O-deoxycytidine (5 mg, ca. 5 µmol) and tetramethylguanidine (TMG, 4 µl, ca. 30 µmol) in acetonitrile (200 µl) were added to the column and reacted for 5 min, followed by washing with acetonitrile (3 mL, 30 s).

Step 2': [Rp]-N4-Benzoyl-5'-O-dimethoxytrityl-3'-O-(5-phenyl-3-N-fluoroacetyl)-1,3,2-oxazaphospholanyl-2'-O-deoxycytidine (FIG. 10B, 5 mg, ca. 5 µmol) and tetramethylguanidine (TMG, 4 µl, ca. 30 µmol) in acetonitrile (200 µl)) were added to the column and reacted for 5 min, followed by washing with acetonitrile (3 mL, 30 s). 3: The resulting product from step 2 or 2' was treated with 3H-1,2-benzodithiol-3-one 1,1-dioxide (1% Beaucage Reagent in acetonitrile (w/v)), 3 min, followed by washing with acetonitrile (3 mL, 30 s).

Step 4: The resulting product from step 3 was capped with acetic anhydride/lutidine/tetrahydrofuran (Applied Biosystems DNA synthesis reagent), (1 mL), mixed with 1-methylimidazole/tetrahydrofuran (Applied Biosystems DNA synthesis reagent), (1 mL), 2 min, followed by washing with acetonitrile (3 mL, 30 s).

Step 5: The trinucleotide can be cleaved from the support and deprotected.

In the present example, a standard column DMT-CBz-LCAA-CPG (0.2 µmol) can be used and subjected to the above steps in the following sequence:

1, 2, 3, 2, 3, 4, 1, 2', 3, 2', 3, 4, 1, 2, 3, 2, 3, 5.

The product obtained in this example can be analyzed by RP-HPLC. P-diastereomeric purity can be confirmed by co-injection of the tetramer prepared in the accordance with this example and the corresponding P-diastereomeric mixture obtained by the standard phosphoramidite method.

Example 17

This example describes the synthesis of a P-diastereomerically pure phosphorothioate-linked undecamer, [all Rp]-(Tps)11T (eleven nucleoside units in the oligonucleotide chain). The following steps were used in the present example.

Step 1: The bound nucleoside was treated with 3% trichloroacetic acid/dichloromethane (Applied Biosystems DNA synthesis reagent), (3 mL, 1 min), followed by washing with acetonitrile (3 mL, 30 s).

Step 2: [Sp]-5'-O-Dimethoxytrityl-3'-O-(5-phenyl-3-N-fluoroacetyl)-1,3,2-oxazaphospholanyl-2'-O-deoxythymidine (5 mg, ca. 5 µmol) and tetramethylguanidine (TMG, 4 µl, ca. 30 µmol) in acetonitrile (200 µl) were added to the column and reacted for 5 min., followed by washing with acetonitrile (3 mL, 30 s).

Step 3: The resulting product from step 2 was treated with 3H-1,2-benzodithiol-3-one 1,1-dioxide (1% Beaucage Reagent in acetonitrile (w/v)), 3 min, followed by washing with acetonitrile (3 mL, 30 s).

Step 4: The resulting product from step 3 was capped with acetic anhydride/lutidine/tetrahydrofuran (Applied Biosystems DNA synthesis reagent), (1 mL), 2 min, followed by washing with acetonitrile (3 mL, 30 s).

Step 5: The trinucleotide can be cleaved from the support and deprotected.

In the present example, a standard column DMT-T-LCAA-CPG (0.2 µmol) can be used and subjected to the above steps in the following sequence:

[1, 2, 3, 2, 3, 4]11, 5.

The product obtained in the present example is believed to be P-diastereomerically pure.

Example 18

Figure 11:
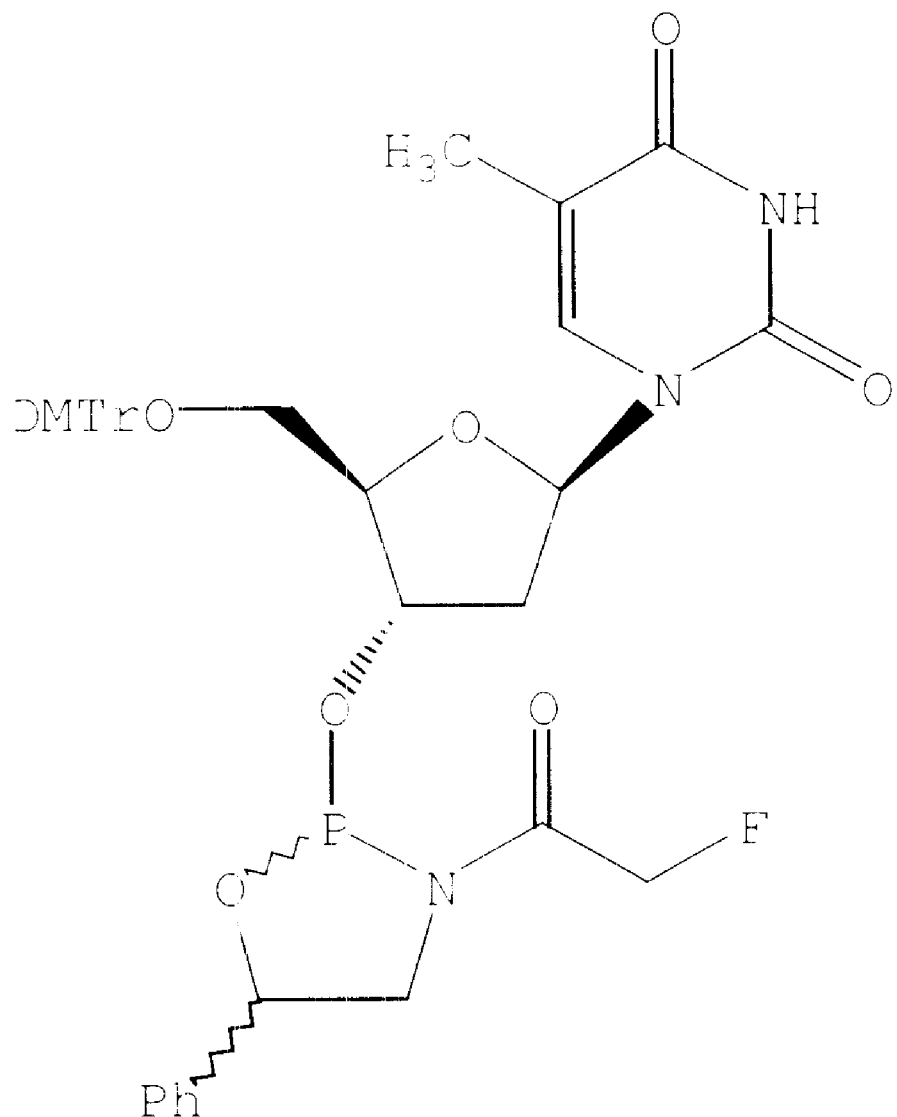
FIG. 11 illustrates the structure of a P-diastereomeric ($R_P$, $S_P$) N-acylphosphoramidite.

This example demonstrates the hydrolytic stability of an N-acylphosphoramidite (FIG. 11), relative to the hydrolytic stability of a corresponding phosphoramidite. The hydrolytic stability for each type of reagent was determined under reaction conditions normally employed for each type of coupling reagent.

Samples of the dinucleotide $d(T_{PO}G)$ were prepared by a standard coupling method using a standard phosphoramidite that is commonly used in the art. Samples of $d(T_{PO}G)$ also were prepared by a coupling reaction using the N-acylphosphoramidite of FIG. 11. Each coupling method was performed in the absence of moisture and in the presence of moisture (0.1% water).

The products were analyzed by HPLC. The HPLC's confirmed that the same product ($d(T_{PO}G)$) was obtained by either method when the reactions were carried out in a moisture-free environment. However, when the same reactions were carried out in the presence of moisture, the product obtained by the standard phosphoramidite contained only a trace of the desired product, and was almost entirely the uncoupled single nucleoside dG. Thus, the standard phosphoramidite was hydrolytically unstable under coupling conditions in which moisture was present. By contrast, the product obtained using the N-acylphosphoramidite (FIG. 11) contained mostly the desired product, and a relatively minor amount of the uncoupled single nucleoside dG, even when the coupling reaction was performed in the presence of significant moisture. These results demonstrate the relative hydrolytic stability of the N-acylphosphoramidites described herein.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of deprotecting an oligonucleotide, which method comprises heating an oligonucleotide of the formula:

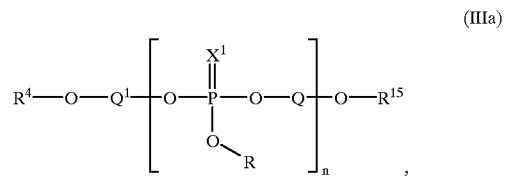

(IIIa)

in a fluid medium, at a substantially neutral pH, at a temperature up to about 100° C. to produce an oligonucleotide of the formula:

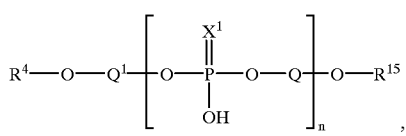

wherein:

R is a thermolabile protecting group of the formula:

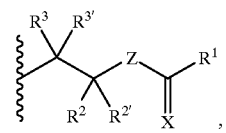

$R^1$ is H, $R^{1a}$, $OR^{1a}$, $SR^{1a}$ or $NR^{1a}R^{1a'}$, wherein $R^{1a}$ and $R^{1a'}$ are the same or different and each is H, an alkyl, an alkenyl, an alkynyl, a cycloalkyl, an aryl, or an aralkyl; or, when $R^1$ is $NR^{1a}R^{1a'}$, $R^{1a}$ and $R^{1a'}$, together with the nitrogen atom to which they are bonded, comprise a heterocycle containing from 3 to about 7 atoms in the ring skeleton thereof;

$X^1$ is O, S or Se;

X is O or S;

Z is O, S, $NR^{2a}$, $CR^{2a}R^{2a'}$ or $CR^{2a}R^{2a'}CR^{2b}R^{2b'}$, wherein $R^{2a}$, $R^{2a'}$, $R^{2b}$ and $R^{2b'}$ are the same or different and each is H, an alkyl, an alkenyl, an alkynyl, a cycloalkyl, an aryl, or an aralkyl; or $R^{1a}$ or $R^{1a'}$, in combination with any of $R^{2a}$, $R^{2a'}$, $R^{2b}$ or $R^{2b'}$, together with C=X of the protecting group to which they are bonded, comprise a ring containing from 3 to about 7 atoms in the skeleton thereof;

provided that $R^1$ is not $R^{1a}$ when Z is S, Z is not $CR^{2a}R^{2a'}$ or $CR^{2a}R^{2a'}CR^{2b}R^{2b'}$ when $R^1$ is $SR^{1a}$, and Z is not O or S when $R^1$ is H;

$R^2$, $R^{2'}$, $R^3$ and are the same or different and each is H, an alkyl, an alkenyl, an alkynyl, a cycloalkyl, an aryl, or an aralkyl, or $R^2$ or $R^{2'}$, in combination wit $R^3$ or $R^{3'}$, together with the carbon atoms to which they are bonded, comprise a cyclic substituent of the formula:

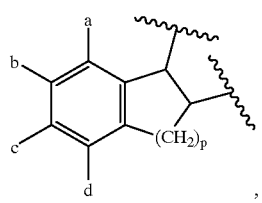

wherein p is an integer from 0–6 and a–d are the same or different and each is selected from the group consisting of H, an alkyl, a nitro, a dialkylamino, an alkoxy, an alkylthio, a cyano and a halogen, provided that the aromatic ring, which bears substituents a–d, is one carbon removed from the phosphate oxygen of formula (IIIa), wherein $R^1$, $R^{2a}$, $R^{2a'}$, $R^{2b}$, $R^{2b'}$, $R^2$, $R^{2'}$, $R^3$ or $R^{3'}$ is unsubstituted or substituted with one or more substituents, which are the same or different, selected from the group consisting of $OR^8$, CN, $NO_2$, $N_3$, and a halogen, wherein $R^8$ is H or an alkyl;

$R^4$ and $R^{15}$ are the same or different and each is H, a hydroxyl protecting group, or a solid support;

$Q^1$ is a nucleoside, an oligonucleotide or an oligomer comprising an oligonucleotide;

n is an integer from 1 to about 300; and

Q is a nucleoside, an oligonucleotide or an oligomer comprising an oligonucleotide and, when n is greater than 1, each Q is independently selected, provided that the deprotection is not by an enzyme.

2. The method of claim 1, wherein Q or $Q^1$ comprises a nucleoside of the formula:

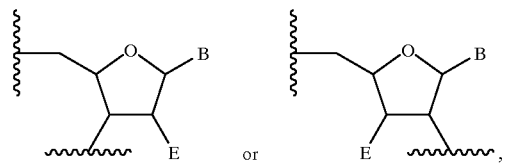

wherein:

B is a labeling group, an alkyl, an alkenyl, an alkynyl, a cycloalkyl, an aryl, a heteroaryl, a heterocycloalkyl, an aralkyl, an amino, an alkylamino, a dialkylamino, a purine, a pyrimidine, adenine, guanine, cytosine, uracil, or thymine, wherein B is unsubstituted or substituted with one or more substituants, which are the same or different, selected from the group consisting of a nucleobase protecting group, $R^{11}$, $OR^{11}$, $NHR^{11}$, $NR^{11}R^{12}$, N=C—$NR^{11'}R^{12'}$, CN, $NO_2$, $N_3$, and a halogen, wherein $R^{11}$ and $R^{12}$ are the same or different and each is H, an alkyl or an acyl, and $R^{11}$ and $R^{12'}$ are the same or different and each is an alkyl or $R^{11'}$ and $R^{12'}$, together with the nitrogen atom to which they are bonded, form a heterocycle containing 3 to about 7 atoms in the ring skeleton thereof; and E is H, a halogen, $OR^{13}$, $NHR^{13}$, or $NR^{13}R^{14}$, wherein $R^{13}$ and $R^{14}$ are the same or different and each is H, a protecting group, an alkyl, or an acyl.

3. The method of claim 1, wherein $R^1$ is H, an alkyl or $NR^{1a}R^{1a'}$, wherein $R^{1a}$ and $R^{1a'}$, together with the nitrogen atom to which they are bonded, comprise a heterocycle containing from 3 to about 7 atoms in the ring skeleton thereof.

4. The method of claim 1, wherein $X^1$ is S.

5. The method of claim 1, wherein Z is $CR^{2a}R^{2a'}$ or $CR^{2a}R^{2a'}CR^{2b}R^{2b'}$ and $R^{2a}$, $R^{2a'}$, $R^{2b}$ and $R^{2b'}$ are the same or different and each is H or an alkyl.

6. The method of claim 1, wherein $R^2$ or $R^{2'}$ is H or an alkyl.

7. The method of claim 1, wherein $R^3$ or $R^{3'}$ is H, an alkyl or an

8. The method of claim 1, wherein R is a protecting group of the formula:

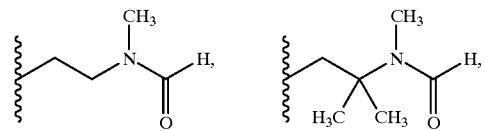

-continued

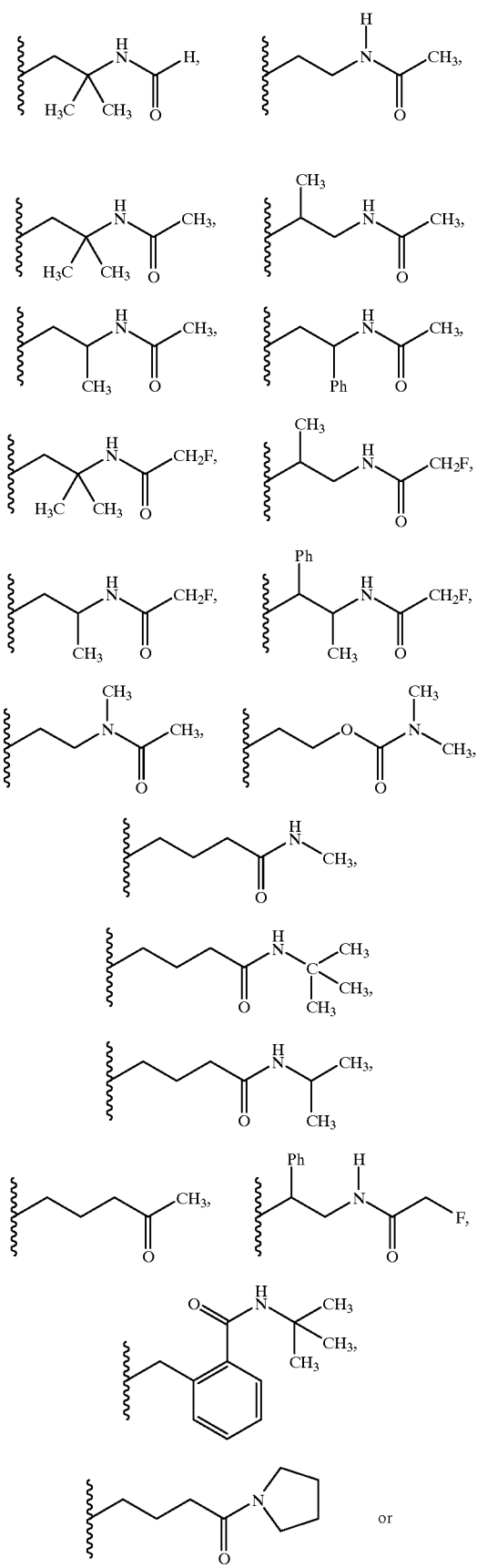

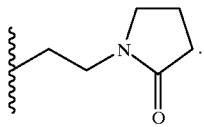

9. The method of claim 1, wherein the temperature is from about 50° C. to about 90° C.

10. The method of claim 1, wherein the deprotection is carried out at about pH 7.

11. The method of claim 1, wherein the fluid medium contains water.

12. A method of producing an oligonucleotide, which method comprises (a) reacting a nucleophile of the formula:

$$R^4-O-Q^1-OH$$

with an electrophile of the formula:

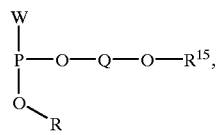

wherein W is a dialkylamino group that is displaced by the nucleophile, under conditions to displace W and produce an adduct comprising a tricoordinated phosphorus atom;

(b) reacting the product obtained in step (a) with a reagent selected from the group consisting of oxidizing agents, sulfurizing agents, and selenizing agents to produce a protected oligonucleotide of the formula:

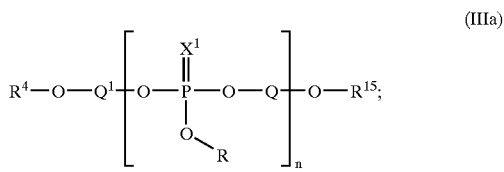

(IIIa)

(c) cleaving $R^{15}$ from the protected oligonucleotide from step (b) to produce a nucleophile;

(d) optionally repeating steps (a)–(c) until an oligomer of a specified length is obtained; and (e) heating the product from step (c) or (d) in a fluid medium, at a substantially neutral pH, at a temperature up to about 100° C. to produce a deprotected oligonucleotide of the formula:

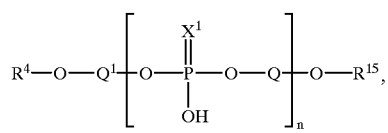

wherein R is a thermolabile protecting group of the formula:

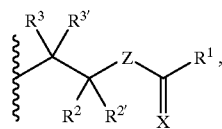

$R^1$ is H, $R^{1a}$, $OR^{1a}$, $SR^{1a}$ or $NR^{1a}R^{1a'}$, wherein $R^{1a}$ and $R^{1a'}$ are the same or different and each is H, an alkyl, an alkenyl, an alkynyl, a cycloalkyl, an aryl, or an aralkyl; or, when $R^1$ is $NR^{1a}R^{1a'}$, $R^{1a}$ and $R^{1a'}$, together with the nitrogen atom to which they are bonded, comprise a heterocycle containing from 3 to about 7 atoms in the ring skeleton thereof;

$X^1$ is O, S or Se;

X is O or S;

Z is O, $NR^{2a}$, $CR^{2a}B^{2a'}$ or $CR^{2a}R^{2a'}CR^{2b}R^{2b'}$, wherein $R^{2a}$, $R^{2a'}$, $R^{2b}$ and $R^{2b'}$ are the same or different and each is H, an alkyl, an alkenyl, an alkynyl, a cycloalkyl, an aryl, or an aralkyl; or $R^{1a}$ or $R^{1a'}$, in combination with any of $R^{2a}$, $R^{2a'}$, $R^{2b}$ or $R^{2b'}$, together with C=X of the protecting group to which they are bonded, comprise a ring containing from 3 to about 7 atoms in the skeleton thereof;

provided that $R^1$ is not $R^{1a}$ when Z is S, Z is not $CR^{2a}R^{2a'}$ or $CR^{2a}R^{2a'}CR^{2b}CR^{2b'}$ when $R^1$ is $SR^{1a}$, and Z is not O or S when $R^1$ is H;

$R^2$, $R^{2'}$, $R^3$ and $R^{3'}$ are the same or different and each is H, an alkyl, an alkenyl, alkynyl, a cycloalkyl, an aryl, or an aralkyl, or $R^2$ or $R^{2'}$, in combination $R^3$ or $R^{3'}$, together with the carbon atoms to which they are bonded, comprise a cyclic substituent of the formula:

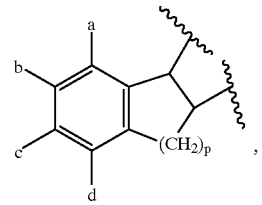

wherein p is an integer from 0–6 and a–d are the same or different and each is selected from the group consisting of H, an alkyl, a nitro, an amino, a hydroxyl, a thio, a cyano and a halogen, provided that the aromatic ring, which bears the substituents a–d, is one carbon removed from the phosphate oxygen of formula (IIIa), wherein $R^1$, $R^{2a}$, $R^{2a'}$, $R^{2b}$, $R^{2b'}R^2$, $R^{2'}$, $R^3$ or $R^{3'}$ is unsubstituted or substituted with one or more substituents, which are the same or different, selected from the group consisting of $OR^8$, CN, $NO_2$, $N_3$, and a halogen, wherein $R^8$ is H or an alkyl;

$R^4$ is H, a hydroxyl protecting group, or a solid support;

$R^{15}$ is a hydroxyl protecting group or a solid support;

$Q^1$ is a nucleoside, an oligonucleotide or an oligomer comprising an oligonucleotide;

n is an integer from 1 to about 300; and

Q is a nucleoside, an oligonueleotide or an oligomer comprising an oligonucleotide and, when a is greater than 1, each Q is independently selected, provided that the deprotection is not by an enzyme.

* * * * *